(12) United States Patent
Berger et al.

(10) Patent No.: US 11,842,017 B2
(45) Date of Patent: Dec. 12, 2023

(54) SECURE KEYBOARD WITH HANDPRINT IDENTIFICATION

(71) Applicants: Jordan A Berger, Stamford, CT (US); John V. Monaco, Pacific Grove, CA (US)

(72) Inventors: Jordan A Berger, Stamford, CT (US); John V. Monaco, Pacific Grove, CA (US)

( * ) Notice: Subject to any disclaimer, the term of this patent is extended or adjusted under 35 U.S.C. 154(b) by 5 days.

(21) Appl. No.: 17/721,362

(22) Filed: Apr. 15, 2022

(65) Prior Publication Data

US 2022/0244800 A1 Aug. 4, 2022

Related U.S. Application Data

(60) Division of application No. 16/558,208, filed on Sep. 2, 2019, now Pat. No. 11,334,197, which is a continuation-in-part of application No. 15/860,690, filed on Jan. 3, 2018, now Pat. No. 10,402,089, which is a continuation-in-part of application No.

(Continued)

(51) Int. Cl.
| | | |
|---|---|---|
| *G06F 3/044* | (2006.01) | |
| *G06F 3/04883* | (2022.01) | |
| *G06F 21/32* | (2013.01) | |
| *G06V 40/13* | (2022.01) | |
| *G06V 40/12* | (2022.01) | |

(Continued)

(52) U.S. Cl.
CPC .............. *G06F 3/044* (2013.01); *A61F 4/00* (2013.01); *G06F 3/04883* (2013.01); *G06F 3/04886* (2013.01); *G06F 21/32* (2013.01); *G06V 40/1306* (2022.01); *G06V 40/1365* (2022.01)

(58) Field of Classification Search
CPC .... G06F 3/0202; G06F 3/0213; G06F 3/0231; G06F 3/044; G06F 3/04883; G06F 3/04886; G06F 21/32; G06K 9/0002; G06K 9/00087
See application file for complete search history.

(56) References Cited

U.S. PATENT DOCUMENTS 5,870,083 A * 2/1999 Shieh .................. G06F 3/04817
  345/157
8,314,775 B2 * 11/2012 Westerman ....... G06F 18/24137
  345/173

(Continued)

*Primary Examiner* — Liliana Cerullo
(74) *Attorney, Agent, or Firm* — Soquel Group LLC

(57) ABSTRACT

A keyboard for physically handicapped persons, including a translucent surface, a capacitive layer underneath the translucent surface, enabling detection of touch location and pressure on the translucent surface, a projection system dynamically projecting a plurality of visual layouts of keys of a keyboard on the translucent surface, wherein each visual layout includes ASCII character keys or graphical buttons, and a dynamic keyboard layout generator configured to receive user input in conformance with a currently projected layout of keys from a physically handicapped user, and to generate therefrom a time series of ASCII characters or button selections for input to the computing device, to dynamically adjust pressure sensitivity of the keyboard to avoid spurious user input, and to dynamically adjust key sizes and positions in a current virtual layout of keys, to reduce the amount of hand motion required by the user and the amount of discomfort experienced by the user.

9 Claims, 19 Drawing Sheets

Related U.S. Application Data

14/809,290, filed on Jul. 27, 2015, now Pat. No. 9,864,516.

(51) Int. Cl.
*A61F 4/00* (2006.01)
*G06F 3/04886* (2022.01)

(56) References Cited

U.S. PATENT DOCUMENTS

2015/0331508 A1* 11/2015 Nho ................. G06F 3/042
    345/173
2017/0212676 A1* 7/2017 Skinner ............ G06V 40/1365

* cited by examiner

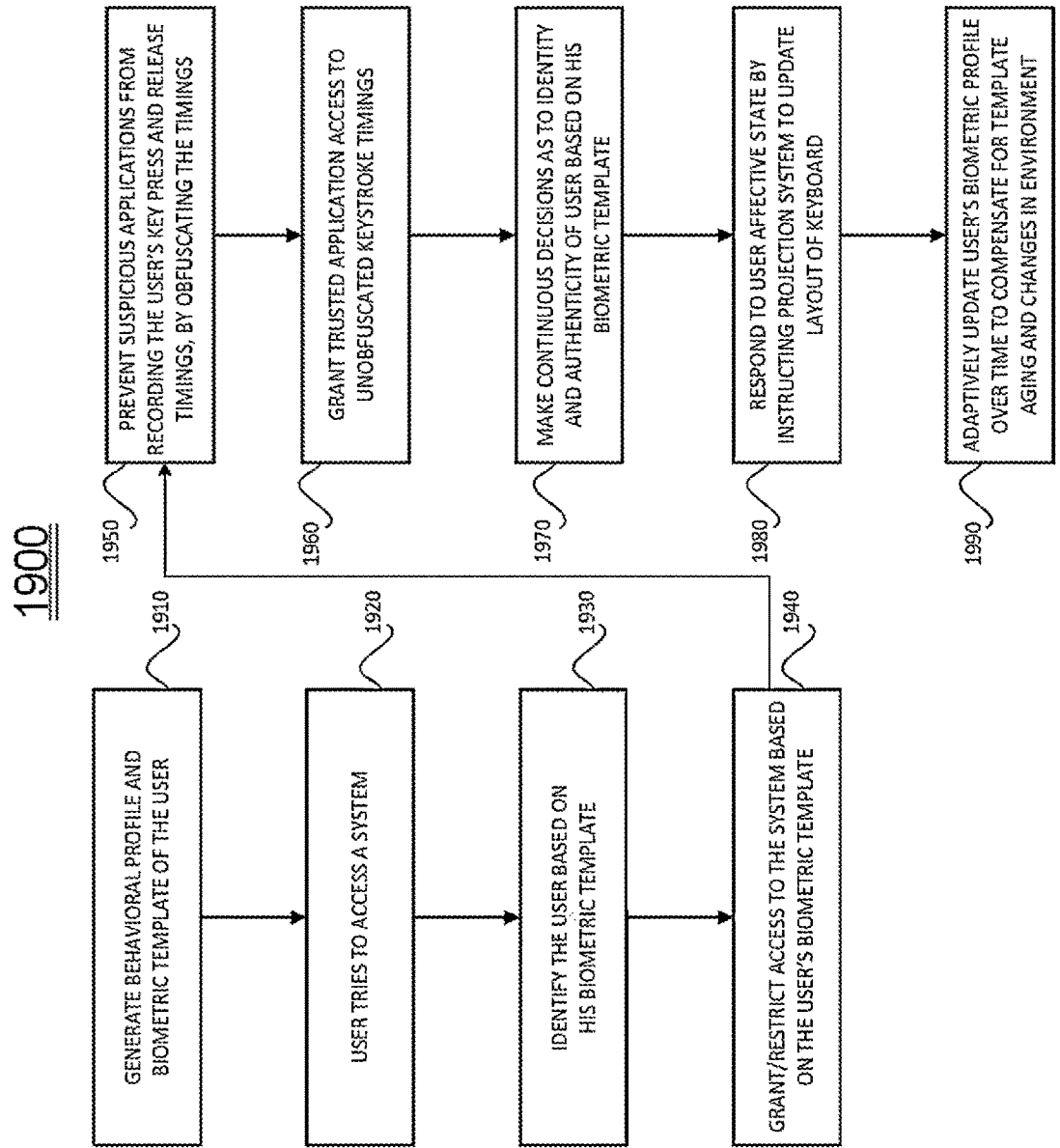

SECURE KEYBOARD WITH HANDPRINT IDENTIFICATION

This application is a divisional of U.S. patent application Ser. No. 16/558,208, now U.S. Pat. No. 11,334,197, entitled UNIVERSAL KEYBOARD, and filed on Sep. 2, 2019 by inventors Jordan A. Berger and John V. Monaco. U.S. patent application Ser. No. 16/558,208 is a continuation-in-part of U.S. patent application Ser. No. 15/860,690, now U.S. Pat. No. 10,402,089, entitled UNIVERSAL KEYBOARD, and filed on Jan. 3, 2018 by inventors Jordan A. Berger and John V. Monaco. U.S. patent application Ser. No. 15/860,690 is a continuation-in-part of U.S. patent application Ser. No. 14/809,290, now U.S. Pat. No. 9,864,516 entitled UNIVERSAL KEYBOARD, and filed on Jul. 27, 2015 by inventors Jordan A. Berger and John V. Monaco.

FIELD OF THE INVENTION

The present invention relates to electronic keyboards.

BACKGROUND OF THE INVENTION

The keyboard is one of the most universal peripheral components for desktop and laptop computers, and yet it relies on the QWERTY system that dates back to the 1870's. It is arguably the most ancient part of the desktop and laptop computers in use today. The use of keyboards is ubiquitous with word processing, web browsing, multimedia streaming and gaming.

Many applications remap keys or key sequences to application-specific commands. For example, "Ctrl+n" creates a new document or opens a new window, depending on the context. The keyboard layout can be entirely remapped through software. The standard QWERTY layout is often associated with a US English key map, but many others exist. For example, some users switch to a DVORAK layout due to comfort, or use a language other than English on a QWERTY keyboard. Many applications allow the user to create time saving "macros", but most users do not take advantage of them due to the high barrier of learning how to program the macros. Users often purchase more than one keyboard or controller, each one made for a specific purpose. For word processing, some users like to use a keyboard with a relatively light touch, but when gaming they prefer a mechanical keyboard with a heavier pressure. Many gaming applications only utilize about 8 keys, and the unused keys become obsolete during gameplay. Many users in the graphics and imaging fields execute thousands of mouse clicks per day to perform tasks that could be highly simplified with a more intelligent human-computer interface.

The current field of keystroke dynamics, as described in
M. Karnan, M. Akila, N. Krishnaraj, Biometric personal authentication using keystroke dynamics: A review, *Applied Soft Computing*, Vol. 11, Issue 2, March 2011, pages 1565-1573, ISSN 1568-4946, http://dx.doi.org/10.1016/j.asoc.2010.08.003, http://www.sciencedirect.com/scient/article/pii/S1568494610000205X,
and
Pin Shen Teh, Andrew Beng Jin Teoh, and Shigang Yue, "A Survey of Keystroke Dynamics Biometrics," *The Scientific World Journal*, Vol. 2013, Article ID 408280, 24 pages, 2013. doi:10.1155/2013/408280,
utilizes behavioral biometric data from users, as described in
Fabian Monrose, Aviel D. Rubin, Keystroke dynamics as a biometric for authentication, *Future Generation Computer Systems*, Vol. 16, Issue 4, February 2000, pages 351-359, ISSN 0167-739X, http://dx.doi.org/10.1016/S0167-739X(99)00059-X, http://www.sciencedirect.com/scient/article/pii/S0167739X9900059X,
in order to perform a variety of important functions, such as on-line user authentication, as described in
Bergadano, Francesco, Gunetti, Daniele, and Claudia Picardi, User authentication through keystroke dynamics, *ACM Transactions on Information and System Security* (*TISSEC*), Vol. 5, issue 4, November 2002, pages 367-397, New York, ACM, ISSN: 1094-9224 EISSN: 1557-7406 doi:10.1145/581271.581272.
Researchers are studying use of keystrokes to detect physical ailments such as arthritis and Parkinson's disease, http://www.nature.com/srep/2015/150409/srep09678/full/srep09678.html).

Keyboards commercially available today are limited in that they can only provide timing information, while it has been shown that use of additional sensors, such as pressure and acceleration, significantly improves the performance of a keystroke biometric system. The demand for additional sensors continues to grow as keystroke dynamics is incorporated into an increasing number of applications.

Prior art virtual keyboards project onto surfaces, and will never likely be a "preferred" keyboard for any user. Virtual keyboards have a futuristic appearance, and can be used in place of keyboards for short sessions, but for the "normal" or "heavy" computer user, the virtual keyboard lacks many features.

Conventional and virtual keyboards can output keystrokes ("all or none") and timing data, but cannot measure pressure data, and lack the spatial resolution that allows, for example, estimation of finger size, limiting their use in advanced behavioral biometrics.

SUMMARY OF THE DESCRIPTION

Embodiments of the present invention relate to a universal keyboard, which is dynamically optimized for all key input to the computer, and is the first fully-compatible biometric keyboard. The keyboard includes a blank translucent surface, a capacitive array touch screen that transmits touch to the computer, and a projection system that dynamically projects the keyboard template or layout that is needed for each application. There are inter alia four types of projection systems: (1) micro-LED array applied to the under-surface of the keyboard, (2) projection system applied to a bar across the keyboard, (3) projection system that projects onto the surface from underneath the keyboard, and (4) touchscreen system.

The universal keyboard includes inter alia a speaker, a microphone, a webcam, an accelerometer, a USB connection, and an optional wireless module such as a BLUETOOTH® module.

The universal keyboard includes a device driver that initializes the keyboard, the projection system, the microphone, the webcam and a touch pad, that initializes a BLUETOOTH® pairing, that loads a sound file, and that dynamically projects a display file onto the keyboard. The driver also maps touch data to ASCII keystroke or bitmap data, as appropriate, formats the keystroke or bitmap data for output, and outputs the data via USB or such other data channel. Data output from the keyboard via the device driver may use a file format and communications protocol that conform to an existing or future standard.

Embodiments of the universal keyboard enable inter alia dynamic keyboard layout, custom keyboard layout, user identification, accessibility adjustments to accommodate physically handicapped persons, biometric authentication, handprint authentication, cryptographic keys for users, and obfuscation to ensure privacy.

There is thus provided in accordance with an embodiment of the present invention a keyboard for a physically handicapped person, including a blank translucent surface for use as an input device, a capacitive layer mounted underneath the translucent surface, enabling detection of touch location and pressure on the blank translucent surface, a projection system dynamically projecting a plurality of visual layouts of keys of a keyboard on the blank translucent surface, wherein each visual layout comprises ASCII character keys or graphical buttons, and an accessibility module, coupled with the capacitive layer, with the projection system, and with a computing device, configured (i) to receive user input in conformance with a currently projected layout of keys from a physically handicapped user, and to generate therefrom a time series of ASCII characters or button selections for input to the computing device, and (ii) to dynamically adapt to the user's style of typing, including dynamically adjusting pressure sensitivity of the keyboard to avoid spurious user input, and dynamically adjusting key sizes and positions in a current virtual layout of keys, to reduce the amount of hand motion required by the user and the amount of discomfort experienced by the user.

There is additionally provided in accordance with an embodiment of the present invention a secure keyboard, including a blank translucent surface for use as an input device, a capacitive layer mounted underneath the blank translucent surface, enabling detection of touch location and pressure on the blank translucent surface, a projection system projecting a visual layout of keys of a keyboard on the blank translucent surface, the visual layout including ASCII character keys and/or graphical buttons, a handprint generator coupled with the capacitive layer that, upon a user placing his hand on the blank translucent surface, generates a user template describing the user's hand, the user template including a list of keyboard surface coordinates and corresponding pressures, and stores the user template, and a handprint analyzer, coupled with the capacitive layer, with the handprint generator, and with a computing device, that authenticates an unknown user who asserts an identity by matching the unknown user's template, currently generated by the handprint generator, to the stored user template for the identity asserted by the unknown user, wherein if no match is found, indicates that the unknown user is not authorized to use the keyboard or not previously enrolled for the keyboard, and if a match is found, receives user input from the unknown user in conformance with the projected layout of keys, and generates therefrom a time series of ASCII characters or button selections for input to the computing device.

There is additionally provided in accordance with an embodiment of the present invention a keyboard, including a blank translucent surface for use as an input device, a capacitive layer mounted underneath the blank translucent surface, enabling detection of touch location and pressure on the blank translucent surface, a projection system projecting a visual layout of keys of a keyboard on the blank translucent surface, the visual layout including ASCII character keys and/or graphical buttons, a handprint generator coupled with the capacitive layer that, upon a user placing his hand on the blank translucent surface, generates a user template describing the user's hand, the user template including a list of keyboard surface coordinates and corresponding pressures, and stores the user template, and a handprint analyzer, coupled with the capacitive layer and with the handprint generator, that identifies an unknown user by comparing the unknown user's template, currently generated by the handprint generator, to a plurality of stored user templates, wherein if a match is not found then the unknown user is not identified.

BRIEF DESCRIPTION OF THE DRAWINGS

The present invention will be more fully understood and appreciated from the following detailed description, taken in conjunction with the drawings in which:

FIG. 19 is a simplified flowchart of biometric analysis and authentication, in accordance with an embodiment of the present invention.

For reference to the figures, the following index of elements and their numerals is provided. Similarly numbered elements represent elements of the same type, but they need not be identical elements.

Figure 1:
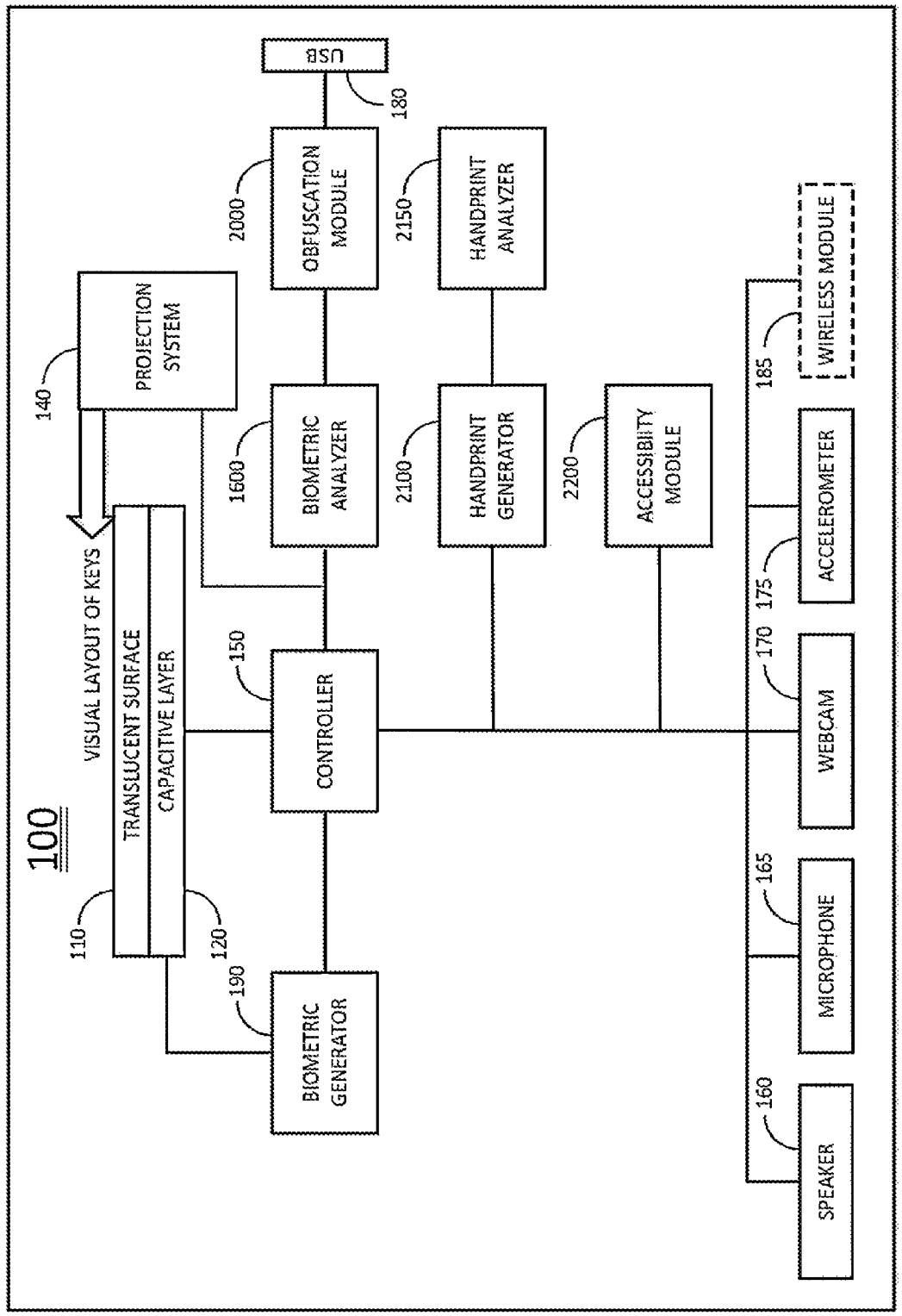
FIG. 1 is a simplified diagram of a keyboard for use in cooperation with a keystroke biometric analyzer, in accordance with an embodiment of the present invention.

Table of elements in the FIGS.

| Element | Description |
|---------|-------------|
| 100 | keyboard |
| 110 | blank translucent surface |
| 120 | capacitive surface |
| 140 | projection system |
| 150 | controller |
| 160 | speaker |
| 165 | microphone |
| 170 | webcann |
| 175 | accelerometer |
| 180 | USB connector |
| 185 | wireless module |
| 190 | biometric generator |
| 200 | keyboard |
| 210 | blank translucent surface |
| 220 | capacitive surface |
| 240 | projection system |
| 250 | controller |
| 260 | speaker |
| 265 | microphone |
| 270 | webcann |
| 275 | accelerometer |
| 280 | USB connector |
| 285 | wireless module |
| 290 | dynamic keyboard layout generator |
| 300 | keyboard |
| 310 | finished acrylic material |
| 320 | alloy bond metal cover |
| 330 | microprocessor |
| 340 | lithium ion battery |
| 350 | micro-USB charging port |
| 360 | LED |
| 410 | silicone layer |
| 420 | touch sensor layer |
| 430 | acrylic layer |
| 440 | LED layer |
| 450 | acrylic blocks |
| 500 | layout of keys |
| 510 | character keys |
| 520 | space bar |
| 530 | cancel key |
| 540 | special character key |
| 550 | copy key |
| 560 | paste key |
| 570 | touch pad |
| 580 | sensitivity scroll bar |
| 600 | layout of keys |
| 610 | character keys |
| 620 | space bar |
| 630 | special keys |
| 640 | keys for language selection |
| 650 | key for adding a language |
| 680 | sensitivity scroll bar |
| 700 | layout of keys |
| 710 | directional keys |
| 720 | special key |
| 730 | special key |
| 740 | special key |
| 750 | special key |

Table of elements in the FIGS.

| Element | Description |
|---------|-------------|
| 800 | method |
| 810 | flowchart operation |
| 820 | flowchart operation |
| 830 | flowchart operation |
| 900 | method |
| 910 | flowchart operation |
| 920 | flowchart operation |
| 930 | flowchart operation |
| 1000 | keyboard driver |
| 1100 | mouse driver |
| 1200 | keyboard embodiment using micro-LED array projection |
| 1210 | silicone layer |
| 1220 | capacitive layer |
| 1230 | acrylic layer |
| 1240 | micro LED layer |
| 1300 | keyboard embodiment using projection bar |
| 1310 | acrylic keyboard |
| 1340 | projection bar |
| 1400 | keyboard embodiment using projection underneath keyboard |
| 1410 | acrylic layer |
| 1420 | support layer |
| 1440 | projection device |
| 1500 | keyboard embodiment using touchscreen |
| 1510 | touchscreen |
| 1600 | biometric analyzer |
| 1610 | biometric identifier |
| 1620 | biometric authenticator |
| 1630 | biometric behavioral analyzer |
| 1640 | biometric learning machine |
| 1700 | keyboard to accommodate users with limited metacarpophalangeal (digits/palm joint) or intercarpal (palm/wrist joint) articulation in the left hand |
| 1800 | keyboard to accommodate users that experience tremors in the hand such as user suffering from Parkinson's disease, and for users with limited motor accuracy such as users recovering from a stroke |
| 1900 | method |
| 1910 | flowchart operation |
| 1920 | flowchart operation |
| 1930 | flowchart operation |
| 1940 | flowchart operation |
| 1950 | flowchart operation |
| 1960 | flowchart operation |
| 1970 | flowchart operation |
| 1980 | flowchart operation |
| 1990 | flowchart operation |
| 2000 | obfuscator module |
| 2100 | handprint generator |
| 2150 | handprint analyzer |
| 2200 | accessibility module |
| 2300 | cryptographic module |

DETAILED DESCRIPTION

Embodiments of the present invention relate to a universal keyboard, referred to herein as the "ONE-KEYBOARD", which is a universal solution to all key input to the computer, and is the first fully-compatible biometric keyboard.

The keyboard consists of a blank translucent surface, a capacitive array touch screen that transmits touch to the computer, and a projection system that projects the keyboard template or layout that is needed for each application. As described below, there are inter alia four types of projection systems: (1) micro-LED array applied to the under-surface of the keyboard, (2) projection system applied to a bar across the keyboard, (3) projection system that projects onto the surface from underneath the keyboard, and (4) touchscreen system.

The ONE KEYBOARD comes in a variety of sizes and in a software-only version. A user has a choice of silicone pads that adhere to the surface of the ONE KEYBOARD, in order to find the preferred "touch". The ONE KEYBOARD is supported on two legs that are adjustable to the user's preferred angle. A small speaker in the keyboard allows the user to choose from a variety of pre-recorded sounds to simulate the "click" of a key and provide minimal haptic feedback. The user can choose a binary sound, which makes a sound at a single decibel level, or variable sounds that are louder or softer depending on the pressure applied to the key. The ONE KEYBOARD comes in wired or wireless (e.g., BLUETOOTH®) models. Both models display the internal circuitry through the acrylic, for aesthetic purposes. The touch sensors may be set to whatever threshold the user prefers, and the threshold may vary based on the application being used. There are optional accessories, including inter alia a mouse, microphone, webcam and speaker.

Reference is made to FIG. 1, which is a simplified diagram of a keyboard 100 for use in cooperation with a keystroke biometric analyzer, in accordance with an embodiment of the present invention. As shown in FIG. 1, keyboard 100 includes a blank translucent surface 110 for use as an input device. Translucent surface 110 may be inter alia a silicone surface. A capacitive layer 120 is mounted underneath translucent surface 110, for enabling detection of touch location and touch pressure on translucent surface 110. A projection system 140 projects a visual layout of keys of a keyboard on translucent surface 110. A controller 150 includes circuitry to control operation of the components of keyboard 100. Keyboard 100 includes a speaker 160, a microphone 165, a webcam 170, an accelerometer 175, and a USB connector 180. Accelerometer 175 measures small movements in the keyboard induced by a user's actions. Keyboard 100 also includes an optional wireless module 185, for short-range wireless communication such as BLUETOOTH®.

Keyboard 100 includes a biometric generator 190 operative to receive user input in conformance with the projected layout of keys, and to generate therefrom a time series of touch location and touch pressure data, for use as data by a keystroke biometric analyzer 1600. Biometric analyzer 1600 is described below with reference to FIG. 16. Keyboard 100 also includes an obfuscation module 2000 for protecting a user's privacy. Obfuscation module 2000 is described below with reference to FIG. 19.

Keyboard 100 also includes a handprint generator 2100 and a handprint analyzer 2150 described below. Keyboard 100 also includes an accessibility module 2200 for users who have difficulty typing on a standard keyboard. Accessibility module 2200 is described below with reference to FIGS. 17 and 18. Keyboard 100 also includes a cryptographic module 2300 that generates a unique cryptographic key for each user, described below.

Figure 2:
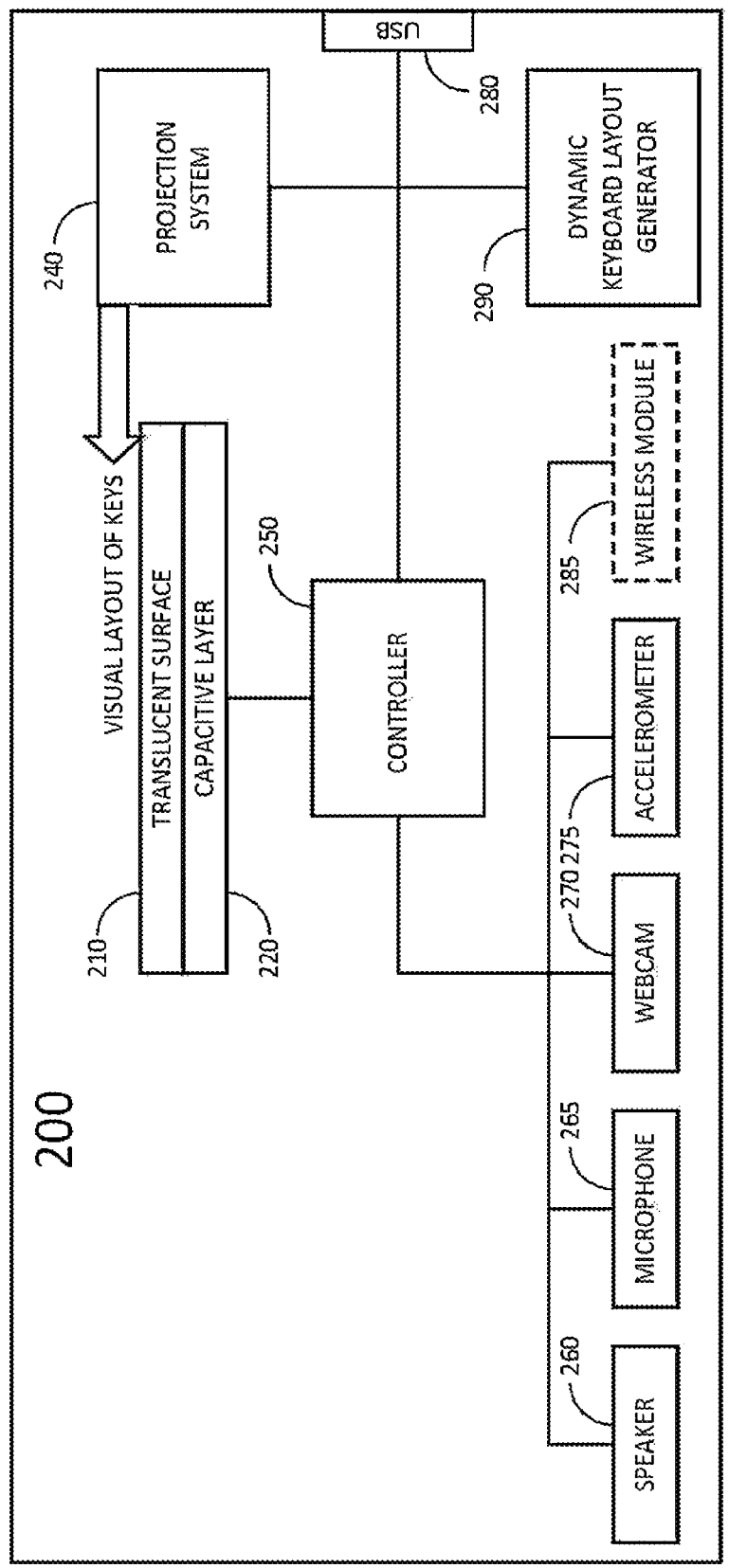
FIG. 2 is a simplified diagram of a keyboard with interactive generation of layouts of keys, in accordance with an embodiment of the present invention.

Reference is made to FIG. 2, which is a simplified diagram of a keyboard 200 with interactive generation of layouts of keys, in accordance with an embodiment of the present invention. As shown in FIG. 2, keyboard 200 includes a blank translucent surface 210 for use as an input device. Translucent surface 210 may be inter alia a silicone surface. A capacitive layer 220 is mounted underneath translucent surface 210, for enabling detection of touch location on translucent surface 210. A projection system 240 dynamically projects a plurality of visual layouts of keys of a keypad on translucent surface 210, where each visual layout includes ASCII character keys or graphical buttons. A controller 250 includes circuitry to control operation of the components of keyboard 200. Keyboard 200 includes a speaker 260, a microphone 265, a webcam 270, an accel-erometer 275, and a USB connector 280. Accelerometer 275 measures small movements in the keyboard induced by a user's actions. Keyboard 200 also includes an optional wireless module 285, for short-range wireless communication such as BLUETOOTH®.

Keyboard 200 includes a dynamic keyboard layout generator 290 operative to dynamically control projection system 240 to project different layouts of keys on translucent surface 210 in response to user activity on a computing device, to receive user input in conformance with a currently projected layout of keys, and to generate therefrom a time series of ASCII characters or button selections for input to the computing device.

It will be appreciated by those skilled in the art that the embodiments shown in FIGS. 1 and 2 may be combined into an embodiment that combines biometric generator 190 with dynamic keyboard layout generator 290.

Figure 3:
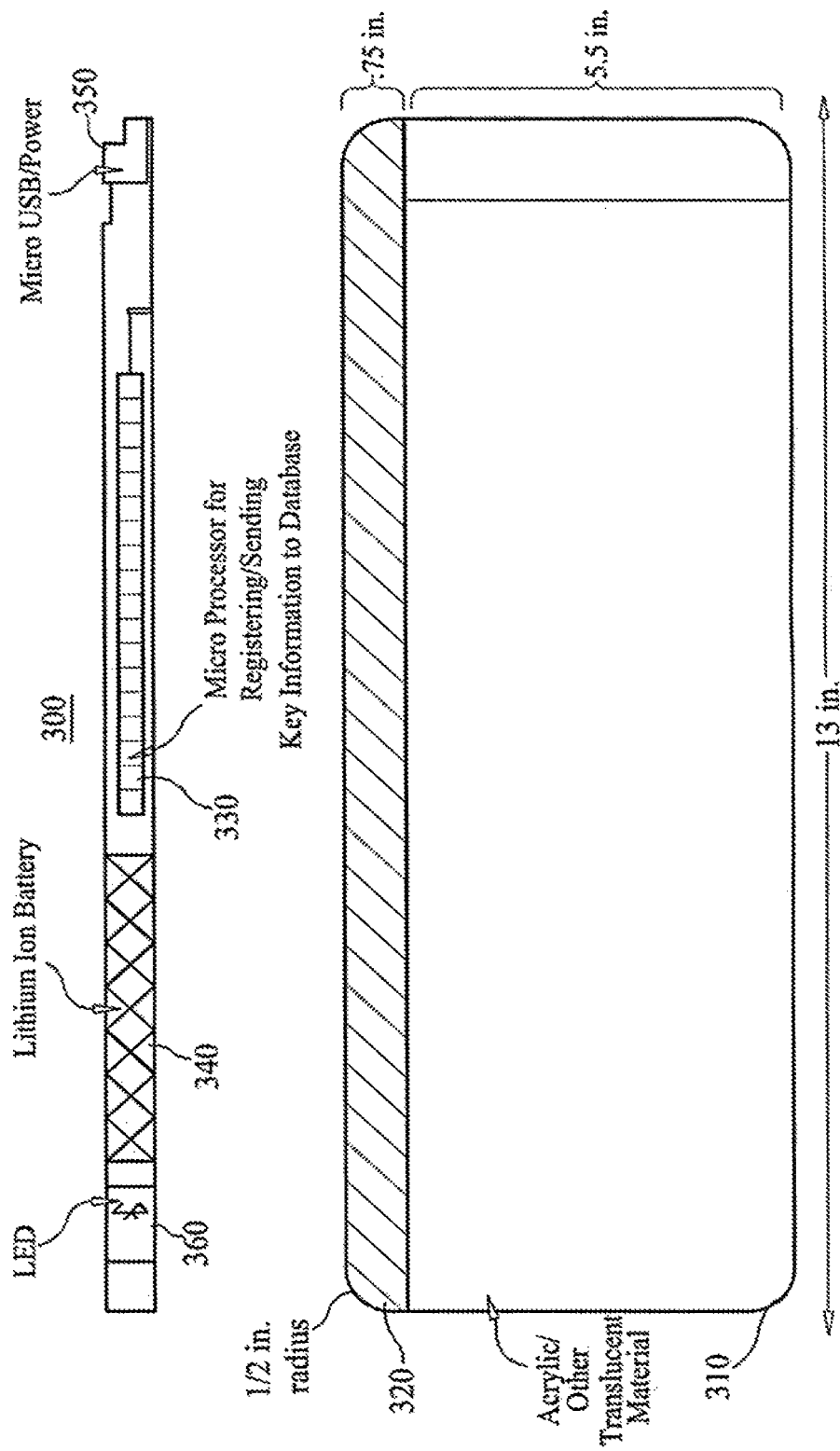
FIG. 3 is a simplified top view of a keyboard, in accordance with an embodiment of the present invention.

Reference is made to FIG. 3, which is a simplified top view of a keyboard 300, in accordance with an embodiment of the present invention. As shown in FIG. 3, keyboard 300 is approximately 13" in length and 5.5" in width, and is formed by an acrylic or other translucent material 310 including inter alia glass, plexi-glass and a combination of such materials. The components of keyboard 300 are covered by an alloy bond metal cover 320 having a width of 0.75", with upper corners curved in an arc of a circle of 0.5" radius. Keyboard 300 includes a microprocessor 330 for registering and sending key information to a database, an 1100 mAh lithium ion battery 340, a micro-USB connector charging port 350, and an LED 360.

Although element 310 is indicated as being an acrylic material, this is not necessary for practice of the invention, and element 310 may alternatively be comprised of glass, plexi-glass or such other translucent material, or a combination of such materials.

Figure 4:
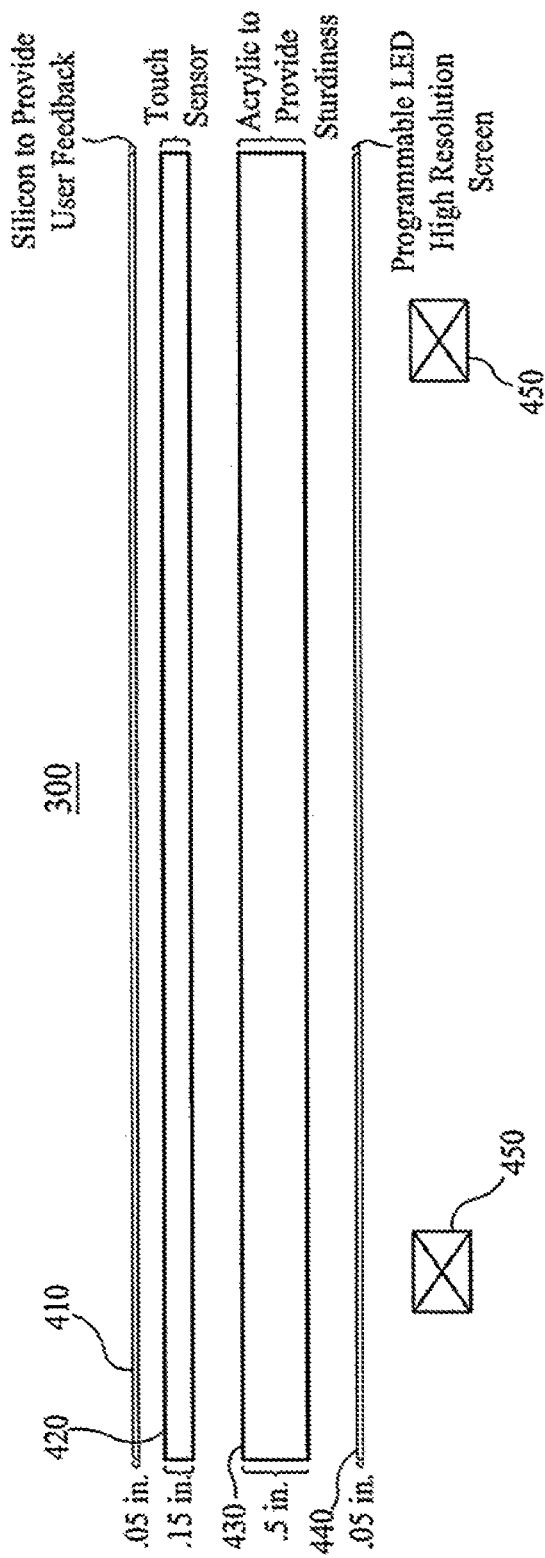
FIG. 4 is a simplified side view of the keyboard of FIG. 3 showing four layers, in accordance with an embodiment of the present invention.

Reference is made to FIG. 4, which is a simplified side view of keyboard 300 showing four layers, in accordance with an embodiment of the present invention. As shown in FIG. 4, keyboard 300 includes an upper layer 410 of silicone having a thickness of 0.05", to provide user feedback. Beneath layer 410 is a layer 420 having a thickness of 0.15" with a touch sensor. Beneath layer 420 is a layer 430 of acrylic having a thickness of 0.5", to provide sturdiness. Beneath layer 430 is a layer 440 having a thickness of 0.05", with a programmable high resolution LED screen. Underneath keyboard 300 are acrylic blocks 450, to angle the keyboard for ease of use.

Figure 5:
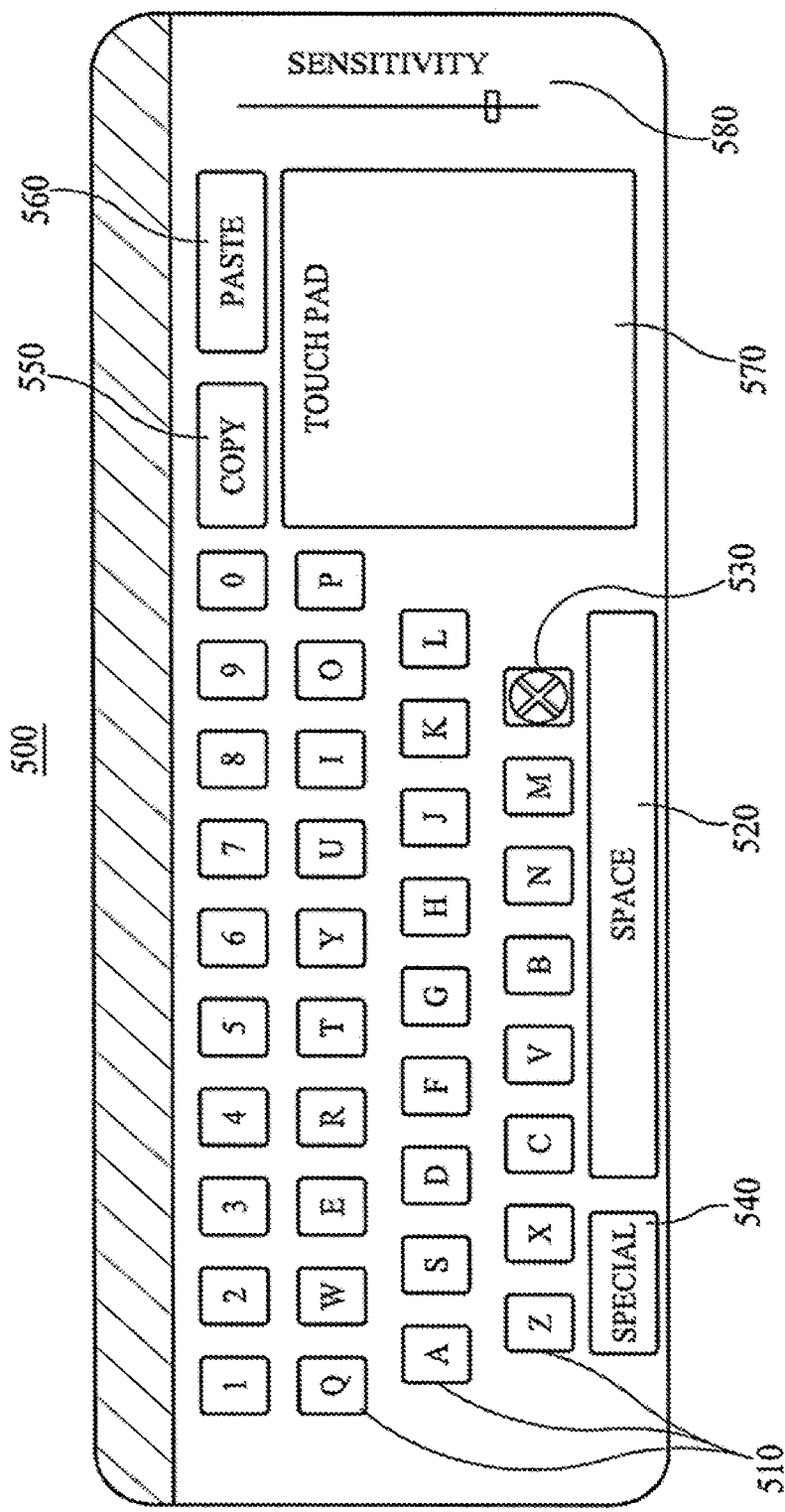
FIG. 5 is a simplified illustration of a layout of keys for word processing, for use with the keyboard of FIG. 3, in accordance with an embodiment of the present invention.

Reference is made to FIG. 5, which is a simplified illustration of a layout of keys 500 for word processing, for use with keyboard 300, in accordance with an embodiment of the present invention. Layout 500 includes QWERTY character keys 510, a space bar 520, a cancel key 530, a special character key 540, and respective copy and paste keys 550 and 560. Layout 500 also includes a touch pad 570, and a scroll bar 580 for touch sensitivity.

Figure 6:
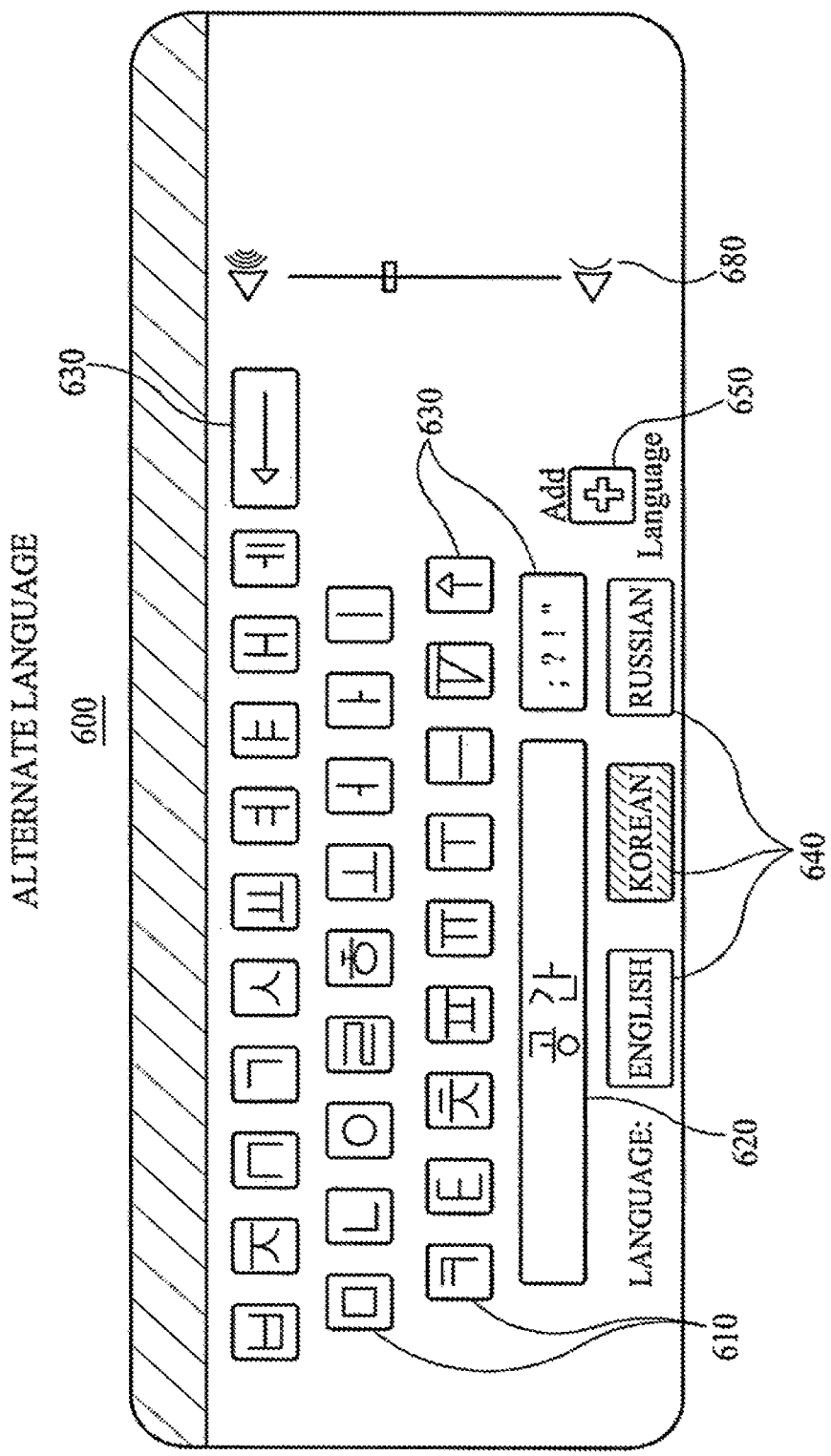
FIG. 6 is a simplified illustration of a layout of keys for an alternate language, for use with the keyboard of FIG. 3, in accordance with an embodiment of the present invention.

Reference is made to FIG. 6, which is a simplified illustration of a layout of keys 600 for an alternate language, for use with keyboard 300, in accordance with an embodiment of the present invention. Layout 600 includes character keys 610 for a Korean alphabet, a space bar 620, special keys 630, and keys 640 for language selection. A key 650 is provided for adding additional languages. Layout 600 also includes a scroll bar 680 for touch sensitivity.

Figure 7:
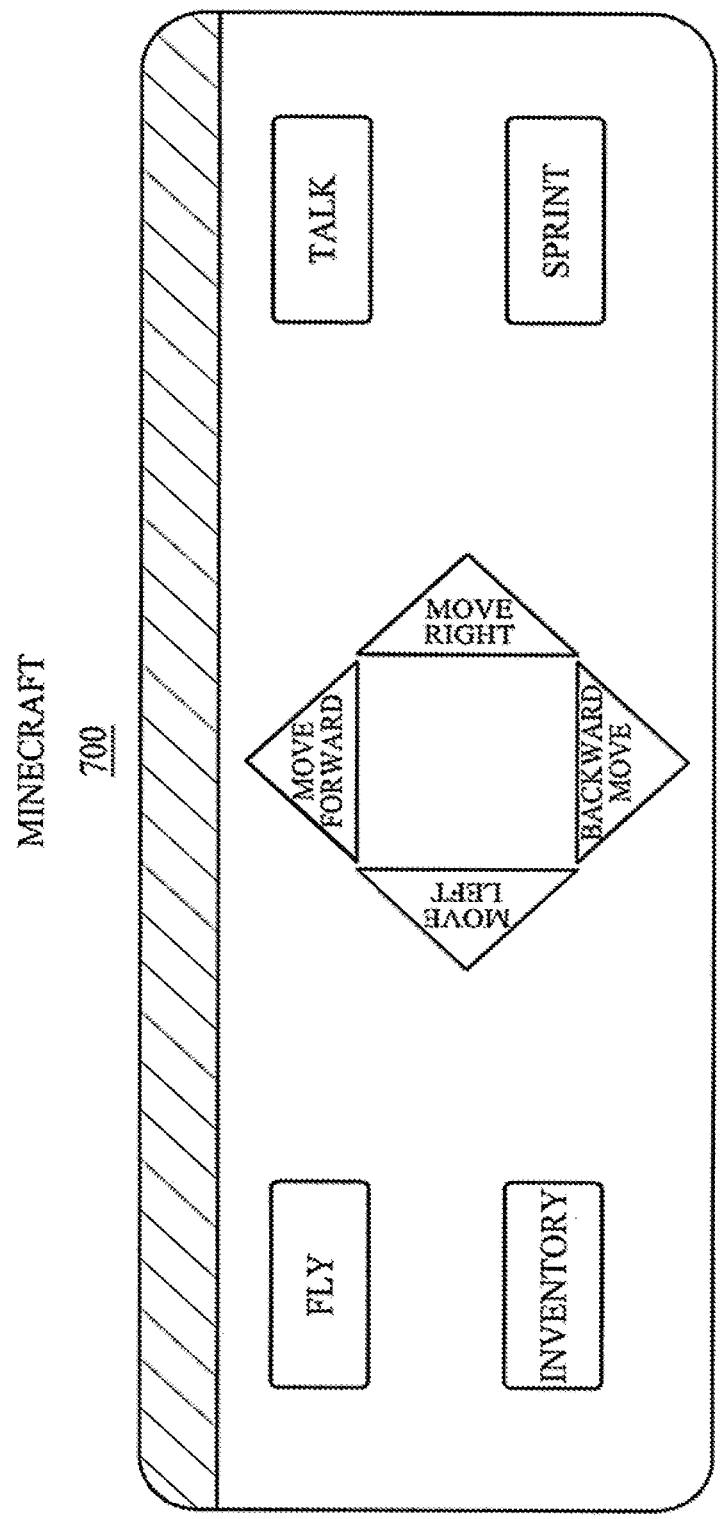
FIG. 7 is a simplified illustration of a layout of keys for an interactive MINECRAFT® game, for use with the keyboard of FIG. 3, in accordance with an embodiment of the present invention.

Reference is made to FIG. 7, which is a simplified illustration of a layout of keys 700 for an interactive MINECRAFT® game, manufactured by Mojang Synergies AB of Stockholm, Sweden, for use with keyboard 300, in accordance with an embodiment of the present invention. Layout 700 includes directional keys 710, and respective keys 720, 730, 740 and 750 for "FLY", "TALK", "INVENTORY" and "SPRINT".

It will be appreciated by those skilled in the art that the layouts 500, 600 and 700 of respective FIGS. 5, 6 and 7, are interactively changed via projection system 240. In particular, both the appearance and the function of the keyboard layout changes dynamically, based on operations performed by a user.

It may thus be appreciated by those skilled in the art that the ONE KEYBOARD supports international and emoji keyboard layouts. Users choose from a list of standard locales, or customize and create a new locale. Thus a bilingual user creates a keyboard layout with keys from both an English QWERTY layout and a French AZERTY layout, or a layout that switches between the two. Embodiments of the present invention include a method that chooses among standard international keyboard layouts, that customizes a standard layout, or that creates a new layout. The size and arrangement of keys on the keyboard surface may be customized by the user through a layout customization program that runs on the ONE KEYBOARD.

Figure 8:
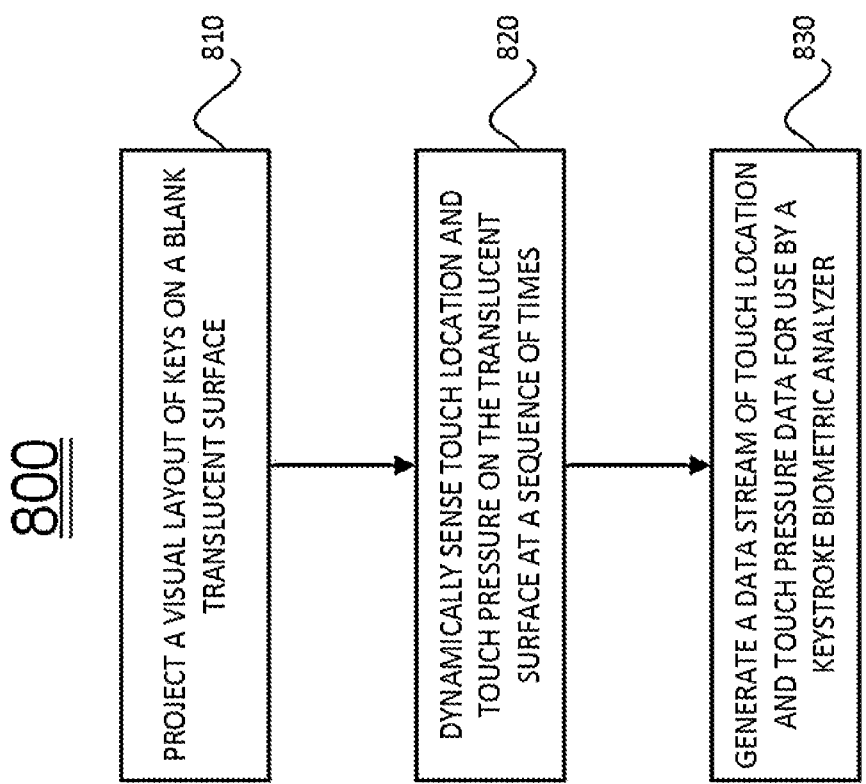
FIG. 8 is a simplified flowchart of a method for using a keyboard to generate data for a keystroke biometric analyzer, in accordance with an embodiment of the present invention.

Reference is made to FIG. 8, which is a simplified flowchart of a method 800 for using a keyboard to generate data for a keystroke biometric analyzer, in accordance with an embodiment of the present invention. At operation 810, projection system 140 (FIG. 1) projects a visual layout of keys onto translucent surface 110. At operation 820, capacitive layer 120 dynamically senses touch location and touch pressure on translucent surface 110 at a sequence of times. At operation 830, biometric generator 190 generates a data stream of touch location and touch pressure data for use by a keystroke biometric analyzer.

Figure 9:
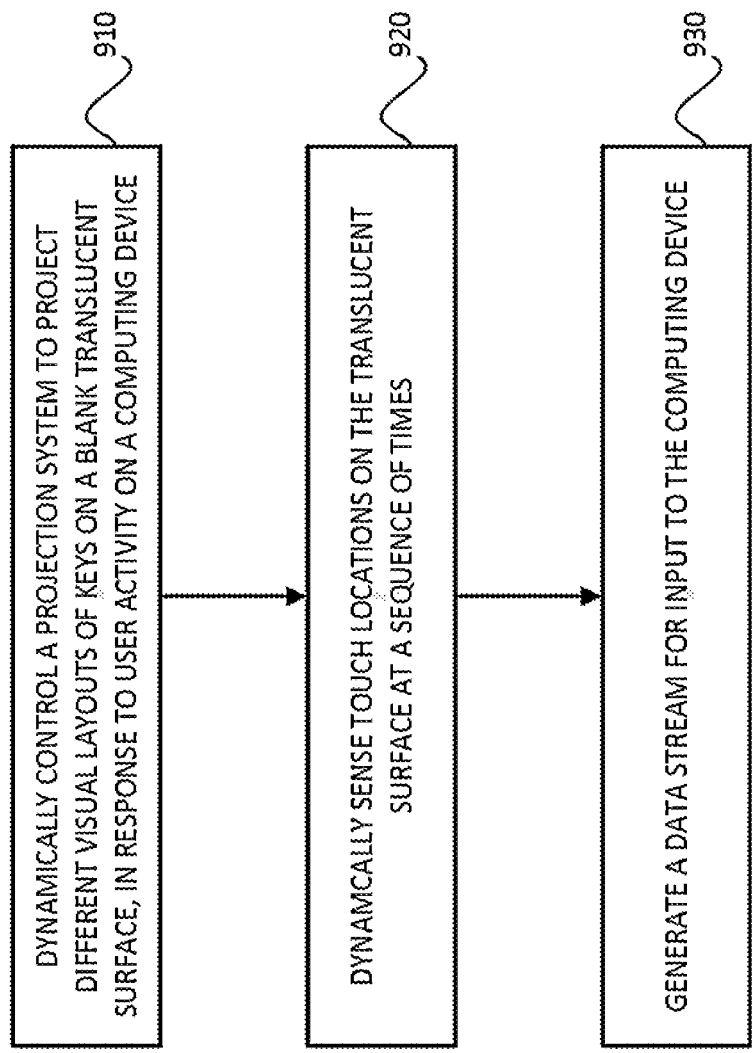
FIG. 9 is a simplified flowchart of a method for interactively generating layouts of keys for a keyboard, in accordance with an embodiment of the present invention.

Reference is made to FIG. 9, which is a simplified diagram of a method 900 for interactively generating layouts of keys for a keyboard, in accordance with an embodiment of the present invention. At operation 910, dynamic keyboard layout generator 290 (FIG. 2) dynamically controls projection system 240 to project different ones of a plurality of visual layouts of keys of a keypad on translucent surface 210, in response to user activity on a computing device, where each visual layout comprises ASCII character keys or graphical buttons. At operation 920, capacitive layer 220 dynamically senses touch locations on the translucent surface at a sequence of times. At operation 930, dynamic keyboard generator 290 generates a data stream, such as a data stream of ASCII characters or button selections, at a sequence of times, for input to the computing device, based on the projected layout of keys and the sensed touch locations, at each time in the sequence.

It will be appreciated by those skilled in the art that the methods shown in FIGS. 8 and 9 may be combined into a method that combines biometric data generation with dynamic keyboard layout generation.

Figure 10:
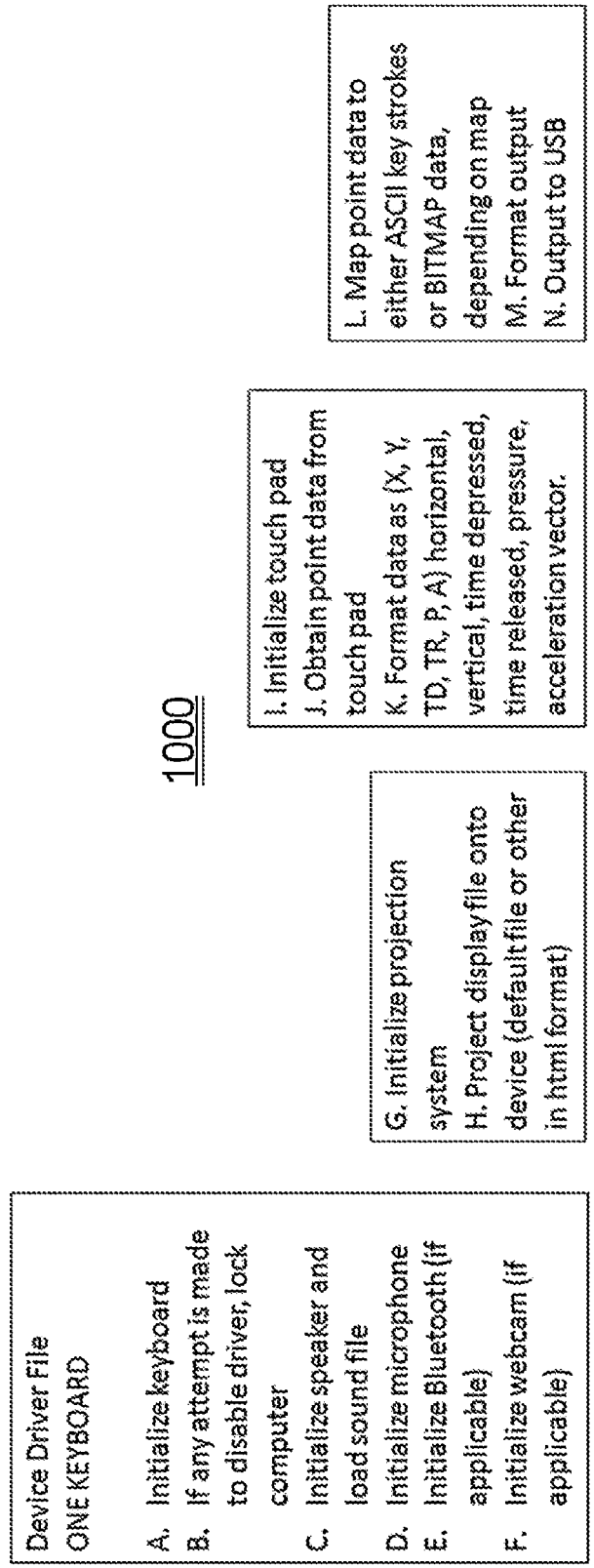
FIG. 10 is a simplified diagram of a keyboard device driver, in accordance with an embodiment of the present invention.

Reference is made to FIG. 10, which is a simplified diagram of a keyboard device driver 1000 for the ONE KEYBOARD, in accordance with an embodiment of the present invention. As shown in FIG. 10, functions of the keyboard driver include inter alia:

A. initializing the keyboard;
B. locking the computer, in response to any attempt to disable the driver;
C. initializing a speaker and loading a sound file;
D. initializing a microphone;
E. initializing a BLUETOOTH® pairing;
F. initializing a webcam;
G. initializing a projection system;
H. projecting a display file onto the keyboard;
I. initializing a touch pad;
J. obtaining a time series of touch data from the touch pad; and
K. formatting the touch data for output as a continuous data stream (X, Y, $T_D$, $T_R$, P, A), where
X is the horizontal location,
Y is the vertical location,
$T_D$ is the time (in milliseconds) that the key is depressed,
$T_R$ is the time (in milliseconds) that the key is released,
P is the pressure (in milligrams) placed upon the key, and
A is the acceleration vector (in m/s$^2$) for small movements in the keyboard induced by a user's actions;
L. map touch data to ASCII keystroke or bitmap data, as appropriate;
M. format the keystroke or bitmap data for output; and
N. output via USB.

Data output from the keyboard via a device driver may use a file format and communications protocol that conform to an existing or future standard. The lowest level output from the ONE KEYBOARD is the continuous data stream of data (X, Y, $T_D$, $T_R$, P, A). In addition, the driver estimates the user's finger size, S, using an edge-detection algorithm, where S is the estimated two-dimensional area of the user's finger as estimated by detecting the diameter, d, of the finger while the key is depressed (e.g., $S=\frac{1}{4}\pi d^2$). The raw pixels covered by the finger are also made available.

When appropriate, touch data is converted (i.e., mapped) onto ASCII keystrokes, and, when needed, the data is converted to graphical data. For example, if the user presses the keyboard where the "J" key is located, the ASCII output for J is sent with the associated pressure measurement; if the user creates a signature on a touchpad, the signature is mapped to a bitmap file, with a corresponding "user pressure matrix", which is a 3D matrix containing the 2D pressure applied along a time axis. The physiology and motor control exhibited by a person's hand is relatively unique and may be used as a form of authentication or identification.

The surface of the ONE KEYBOARD is capable of sensing shape and pressure. As a form of authentication or identification, a user can place his hand on the keyboard surface. Embodiments of the present invention include handprint generator 2100 (FIG. 1) that, upon a user placing his hand on the surface of the keyboard, generates a time series including the times of interaction of the hand with the keyboard surface, the locations of the interaction at each time of interaction, the amount of pressure applied to the keyboard surface at each location and time of the interaction, and the acceleration experienced by the keyboard at each time of interaction. This time series contains information from which physiological measurements are extracted, including finger lengths, palm surface area, and curvature of the hand arches. Behavioral measurements are also extracted, including a pressure heatmap formed by the hand on the keyboard surface, the first and last parts of the hand extremity to make contact with the keyboard surface, and vibrations experienced by the keyboard while the hand is held on the keyboard surface. Together, the time series and these measurements form a template that is provided to the handprint analyzer that runs either on the computing device of the ONE KEYBOARD or is remotely accessible through the ONE KEYBOARD driver software.

Handprint analyzer 2150 (FIG. 1) performs both authentication and identification functions. To authenticate a user, handprint analyzer 2150 matches a user's handprint template to a previously-stored template, to determine whether the user belongs to a list of authorized users. To identify a user, handprint analyzer 2150 matches a user's handprint template to a template contained in a database of previously-stored templates, or fails to make a match if none is found. These functions may be performed at the request of an application running on the host computer, such as at the time of login to a website. The matching of both the authentication and identification functions is performed by measuring the similarity of two templates, considering together the similarity of the respective time series', the physiological measurements, and the behavioral measurements.

Keyboard device driver 1000 may be implemented in software, firmware, hardware, or a combination of software, firmware and hardware.

Figure 11:
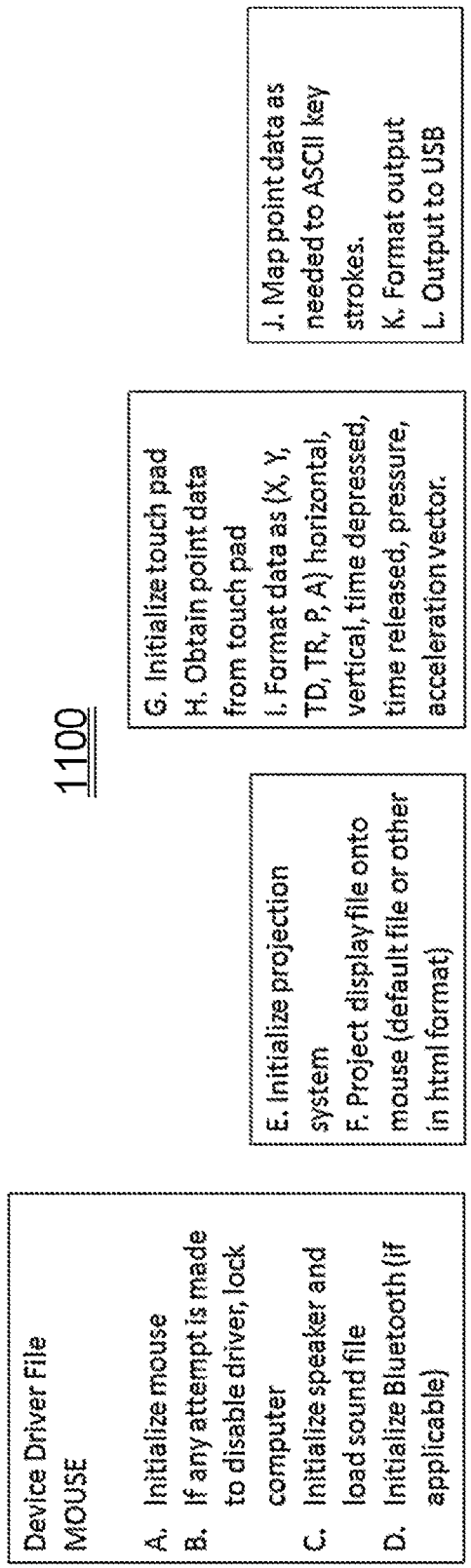
FIG. 11 is a simplified diagram of a mouse device driver, in accordance with an embodiment of the present invention.

Reference is made to FIG. 11, which is a simplified diagram of a mouse device driver 1100, in accordance with an embodiment of the present invention. The mouse that accompanies the ONE KEYBOARD is essentially a miniature version of the keyboard, and is incorporated into the same application. Many optical mouse devices have been created with more than one button or wheel, such as the gaming mice (http://www.razerzone.com/gaming-mice) manufactured by Razer Pte Ltd of Singapore, and such as the MAGIC MOUSE® (http://www.apple.com/magicmouse/) manufactured by Apple Inc. of Cupertino, CA, in order to facilitate the user's interaction with programs that require the same operations over and over again. This is popular in the gaming community. As another example, a radiologist uses the same features of "Zoom", "Pan", "Window" and "Level" to interpret 50 or 100 medical images a day. At this time, he can either use the same repetitive mouse clicks, or try to find a mouse with some added buttons; the mouse that accompanies the ONE KEYBOARD creates a custom panel of buttons. For anyone who does work that requires repetitive tasks, the mouse that accompanies the ONE KEYBOARD is a highly ergonomic solution. The mouse displays user-definable buttons, and collects a small subset of biometric data.

Mouse device driver 1100 may be implemented in software, firmware, hardware, or a combination of software, firmware and hardware.

The ONE KEYBOARD employs a projection system to dynamically adapt a layout of keys to the user's application. If the user is typing a document, the projected layout of keys conforms to a standard keyboard, and switches between languages, mathematical symbols and graphics, as needed. For a user who uses more than one language, the projected layout of keys includes keys in any language, and further includes a "Translate" button that enables the user to type in one language and have it translated to another language. There are hundreds of keyboard layouts being used throughout the world today, any of which may be projected on the ONE KEYBOARD, and the projected keys may be a single color, or may be color-coded, or may be any other design. When the user is working on a photo-book, for example, with a website such as SHUTTERFLY®, owned by Shutterfly, Inc. of Redwood City, CA, the ONE KEYBOARD projects a section that shows inter alia a "Page Layout" button, a "Background" button, an "Add-a-Page" button, a "Theme" button, and a "Color" button. When the user adds photos to the book, the ONE KEYBOARD projects a section that shows inter alia an "Add Photos from Computer" button, an "Add Photos from Shutterfly" button, and an "Add Photos from Instagram" button. There are icons of photos, text and other objects that the user may drag into his book. The user may use gestures to edit a photo, resize the photo, change the contrast, brightness, hue, saturation, and make other adjustments. When the user switches between applications, such as working on a document, and then opening an Internet browser to look something up for the document, the keyboard switches between modes optimized for each application, and produces a set of custom buttons such as "Copy", "Paste" and "Create Hyperlink", to facilitate the interaction between applications. The keyboard works in a highly synchronized fashion with the user, creating the correct keys and icons for each application, and eliminating the need for hundreds of mouse clicks. If authentication is needed, the collected biometric data is used to verify the identity of the user using an external biometric analyzer.

As described below, there are inter alia four embodiments of projection systems: (1) micro-LED array applied to the under-surface of the keyboard, (2) projection system applied to a bar across the keyboard, (3) projection system that projects onto the surface from underneath the keyboard, and (4) touchscreen system.

Figure 12:
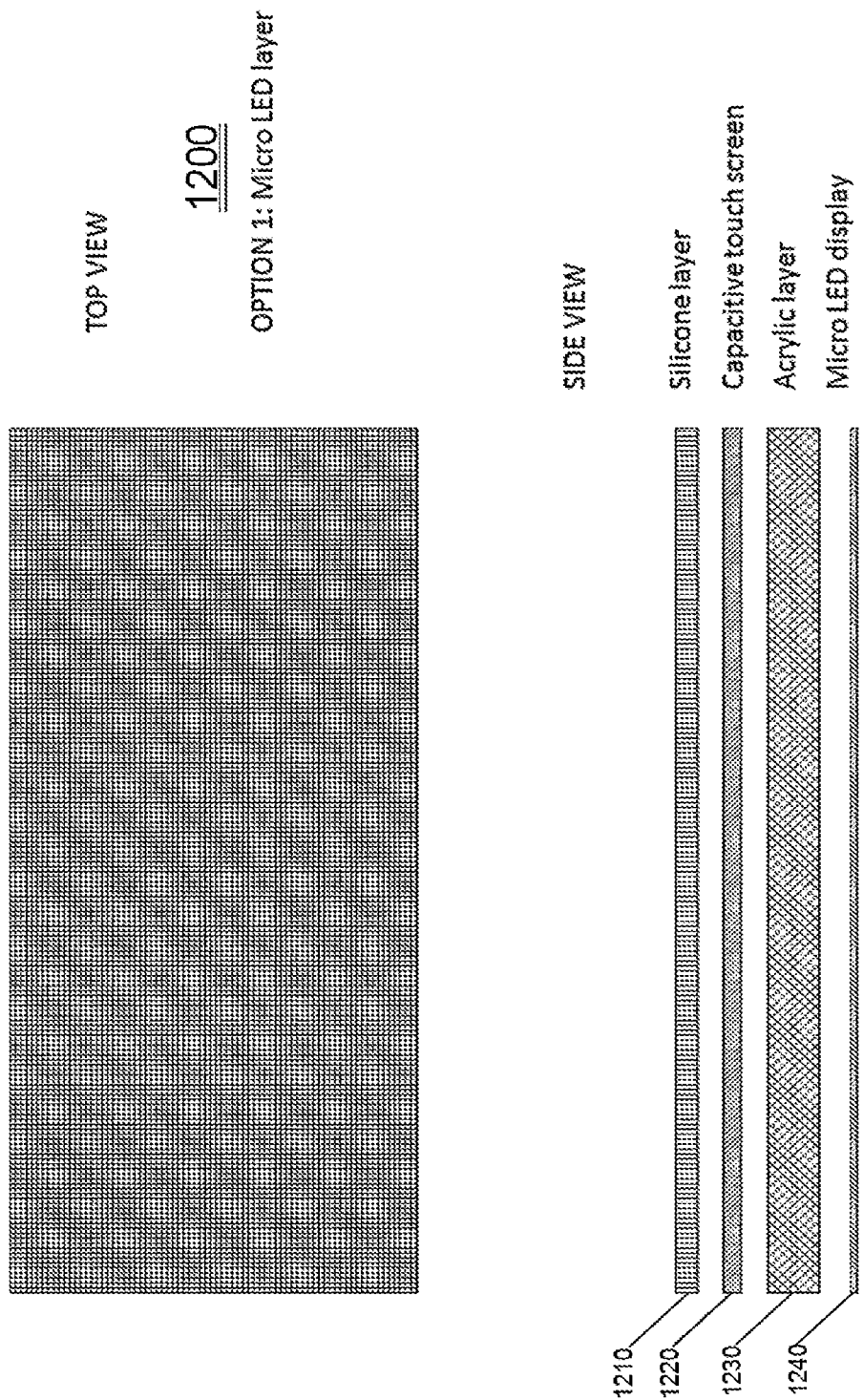
FIG. 12 is a simplified diagram of a keyboard using a micro-LED array projection system, in accordance with an embodiment of the present invention.

Reference is made to FIG. 12, which is a simplified of a keyboard 1200 using a micro-LED array projection system, similar to keyboard 300 shown in FIG. 4, in accordance with a first embodiment of the present invention. Shown in FIG. 12 is a silicone surface 1210, exposed for touch by a user. Underneath silicone surface 1210 is a capacitive touch layer 1220, for detecting touch location and touch pressure when a user touches silicone surface 1210. Underneath capacitive touch layer 1220 is an acrylic layer 1230.

A pattern of keys is projected onto silicone surface 1210 by a micro LED array 1240, underneath acrylic layer 1230.

A controller (not shown) receives user input in conformance with the projected layout of keys, and generates a time series of touch location and touch pressure data therefrom. The touch location and pressure data may be used inter alia by a keystroke biometric analyzer, as explained below.

Figure 13:
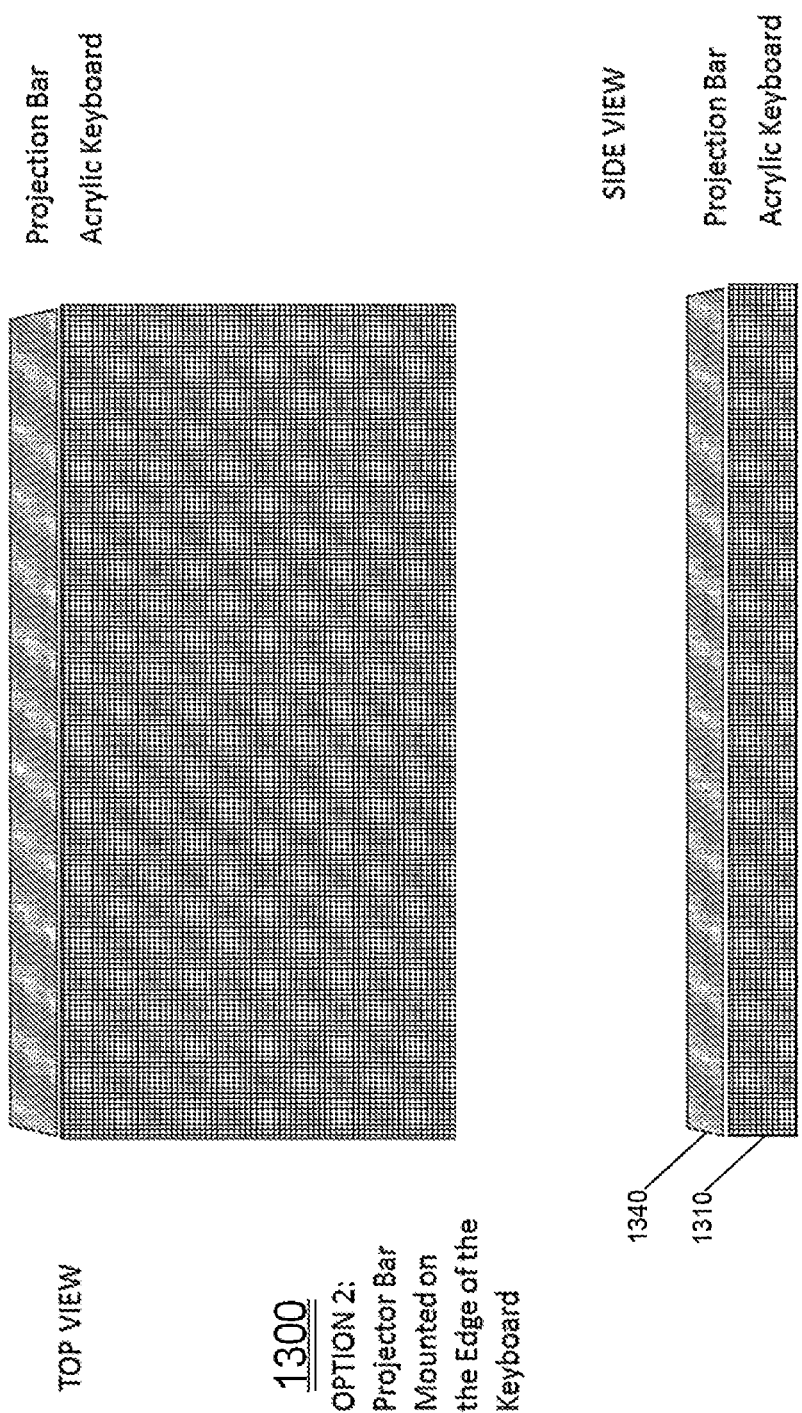
FIG. 13 is a simplified diagram of a keyboard using a projection system applied to a bar across the keyboard, in accordance with an embodiment of the present invention.

Reference is made to FIG. 13, which is a simplified diagram of a keyboard 1300 using a projection system applied to a bar across the keyboard, in accordance with an embodiment of the present invention. Shown in FIG. 13 is an acrylic keyboard 1310 with a projection bar 1340.

Figure 14:
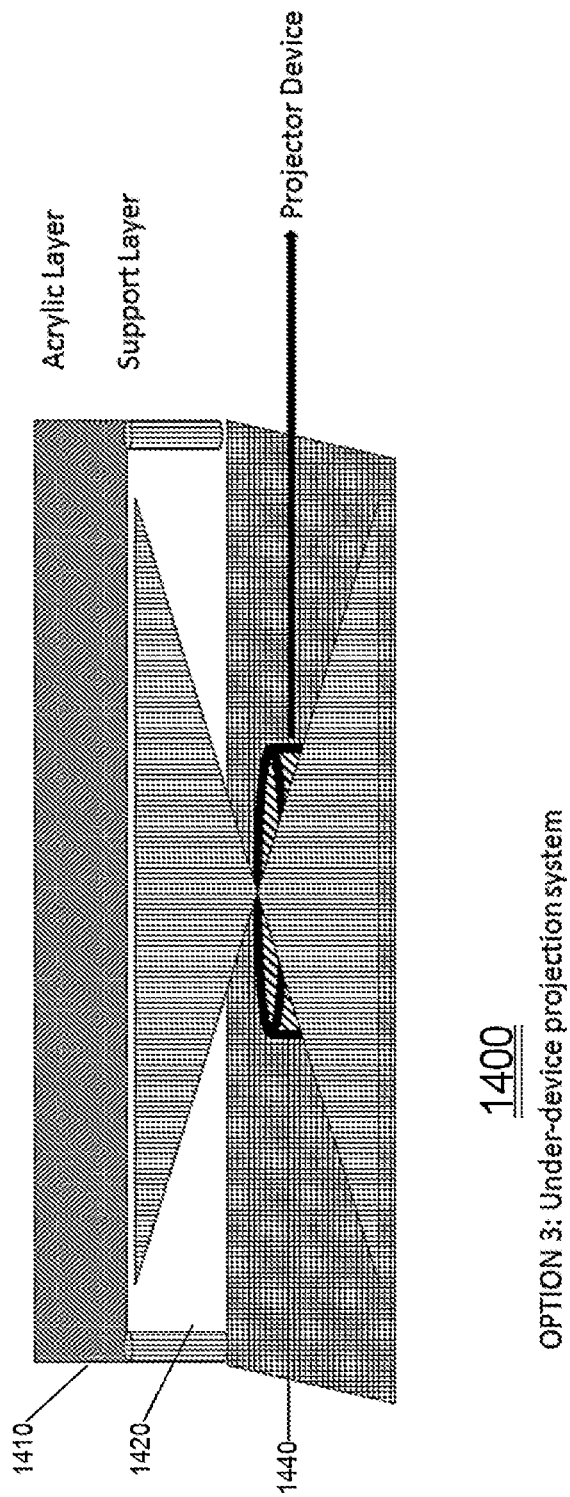
FIG. 14 is a simplified diagram of a keyboard using a projection system that projects onto the surface from underneath the keyboard, in accordance with an embodiment of the present invention.

Reference is made to FIG. 14, which is a simplified diagram of a keyboard 1400 using a projection system that projects onto the surface from underneath the keyboard, in accordance with an embodiment of the present invention. Shown in FIG. 14 is an acrylic surface 1410. A support layer 1420 is underneath acrylic surface 1410. Within support layer 1420 is a projector device 1440, which projects a pattern of keys onto acrylic surface 1410.

Figure 15:
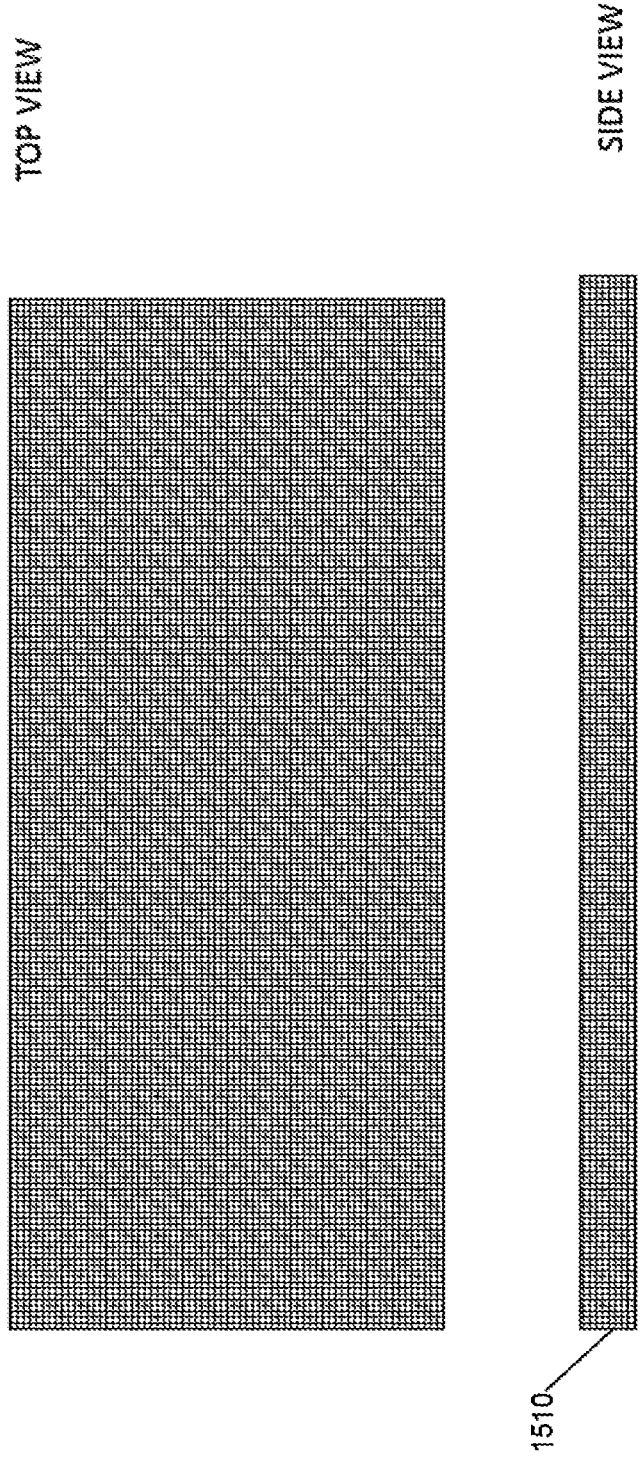
FIG. 15 is a simplified diagram of a keyboard using a touchscreen, in accordance with an embodiment of the present invention.

Reference is made to FIG. 15, which is a simplified diagram of a keyboard 1500 using a touchscreen, in accordance with an embodiment of the present invention. Keyboard 1500 uses a touch pad 1510.

Two or more of the projection systems of FIGS. 12-15 may be combined together into a multi-projection keyboard.

One of the central features of the ONE KEYBOARD is that it uses behavioral biometrics to learn the touch patterns of every individual, via a process termed "keystroke dynamics". This is a security feature to supplement conventional means of authentication, such as username and password, and may also be used as a form of error correction. At the basic level, the device registers the behavioral data associated with each time the user touches the keyboard. Over a short period of time, the data gathered creates a "behavioral profile" for the user. The behavioral profile is the set of numeric and categorical features that describe the keyboard usage history, including key press and release timings, pressure, acoustics, keyboard motion, and the shape of the finger mapped onto a two-dimensional space. From the behavioral profile, biometric information can be extracted to create a "biometric template". The biometric template is a reduced set of features that are highly reproducible and specific for each individual. E.g., the pressure and finger shape may be used to uniquely identify a particular user with high probability. Some of the variations in pressure and finger shape between different users can be attributed to (a) physical traits of the user, such as finger size and strength, (b) the distance from the center of the keyboard, and (c) the user's typing proficiency. Once created, the template is a valuable part of the system. The biometric template may be used to grant and restrict access to a system, identify the keyboard owner, and generate a unique encryption key that can be used to digitally sign documents.

Figure 16:
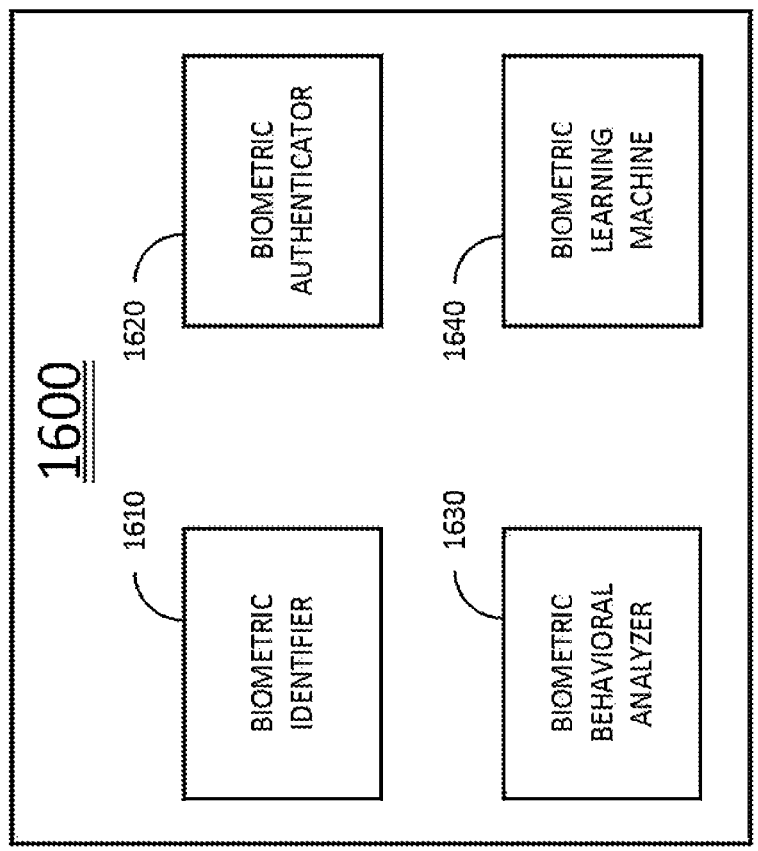
FIG. 16 is a simplified diagram of the biometric analyzer of FIG. 1, in accordance with an embodiment of the present invention.

Reference is made to FIG. 16, which is a simplified diagram of biometric analyzer 1600, in accordance with an embodiment of the present invention. As shown in FIG. 16, biometric analyzer 1600 includes four primary components; a biometric identifier 1610, a biometric authenticator 1620, a biometric behavioral analyzer 1630, and a biometric learning machine 1640.

Biometric identifier 1610 generates and stores the user's biometric template, which represents the unique and identifiable behavior attributes of the user. As the user's behavior changes over time, such as due to increased typing proficiency, typing impairments, and changes in physiology, the biometric template is updated. This is necessary so as to mitigate the "template aging effect", a phenomenon encountered in biometrics in which the user's biometric template becomes less effective over time. Biometric learning machine 1640 implements an online learning mechanism to adapt to these changes in the user's behavior and to respond robustly to changes in the environment, such as keyboard positioning and ambient noises or vibrations.

Biometric authenticator 1620 operates in two modes: static and continuous. In static mode, an authentication or identification decision is made at discrete points in time using all available information up to that point, such as at the beginning of a session or logging into a website. In continuous mode, an authentication or identification decision is made continuously as the user interacts with the keyboard; for authentication decisions in this mode, the biometric authenticator chooses to either allow the session to continue, deeming the user as genuine, or blocks the user from the session, deeming the user as an impostor. For identification decisions in this mode, the keyboard continuously recognizes the identity of the active user, such as in a shared multi-user environment.

"Affective computing" is a field of study that aims to build systems capable of detecting and responding to the user's affect, or emotional state. In a desktop or laptop environment, the ability to detect the user's affective state can enable a more integrated and productive environment. Biometric behavioral analyzer 1630 recognizes the affective state of the user from the recorded behavior profile in order to provide a more robust and dependable computing environment. Affective states and possible responses include inter alia:

| Affective State | Response |
|---|---|
| stress | dynamically adjusting the keyboard interface to decrease user workload and increase productivity |
| frustration | dynamically optimizing the keyboard interface to reduce errors; and confusion dynamically adjusting the keyboard interface to provide assistance and additional relevant information |

With the user's behavioral profile, the ONE KEYBOARD improves workflow. Based on patterns gleaned from the user's experience, the ONE KEYBOARD corrects common mistakes made repeatedly by the user, and suggests moving the position or layout of various aspects of the keyboard for improved comfort. By determining the size of a user's fingers, and the type and number of errors made by the user, the ONE KEYBOARD suggests changes in the layout of keys that can improve the user's experience. E.g., a larger set of keys may be more efficient for certain users. On a wider scale, a company may utilize aggregated behavioral profile data to identify patterns among large numbers of employees that might be slowing productivity. A cloud-based system, when applied to the user profile data, determines ways to improve workflow in a widely used program, for example, such as PHOTOSHOP®, developed and marketed by Adobe Systems of San Jose, CA Software developers may desire the ability to study aggregated behavioral data in order to improve the development of their next generation of applications.

The ONE KEYBOARD is designed to accommodate users who have difficulty typing on a standard keyboard. This includes users who suffer from Parkinson's disease, traumatic brain injury (TBI), or another physical injury that makes standard keyboards inaccessible. These ailments may result in uncontrollable movement of the hand, restricted motor capability in the hand or wrist, or inability to strike certain keys due to loss of appendages. Embodiments of the present invention include a method that adapts and optimizes the layout of the keyboard based on the user's physical condition. The sensitivity of the keyboard is automatically or manually adjusted to avoid spurious input and to adapt to the user's style of typing. Key sizes and positions are adjusted automatically or manually to reduce the amount of hand motion required and the amount of discomfort experienced by the user, as well as to reduce typing errors.

The automatic function is performed by an accessibility module that either runs on the computing device of the ONE KEYBOARD or is remotely accessible through the ONE KEYBOARD driver software. The accessibility module continuously monitors keyboard usage, including typing errors, identification of the appendage (finger, palm, knuckle) used to provide input, position of the appendage on the keyboard surface, and pressure applied to the keyboard surface. The accessibility module infers the user's intent during typing, such as the key the user intended to press, the word the user intended to type, or the shortcut action the user intended to perform within an application. These inferences are made based on: the application context, for example the likelihood of a copy action (typically invoked by Ctrl-V on QWERTY keyboard layouts) to occur following the selection of text with the mouse pointer; natural language constraints, including word spelling, grammar rules, sentence structure, and word frequency; and the user's typing history, including the user's style of writing and the frequent typing of personal information, such as name, address, phone number, email address, and commonly typed phrases. The accessibility module provides shortcuts to quickly invoke the user's intent and adjust keyboard layout so as to minimize typing errors, decrease hand and finger motion, and to avoid uncomfortable or impossible hand positions. For some users, pressing the keyboard surface may itself be a difficult action to perform. For these users, the ONE KEYBOARD supports alternate input methods that eliminate such an action, such as the ability to recognize hand-drawn symbols drawn on the keyboard surface or the mapping of gestures, such as sliding a closed fist in a leftward direction, to keys or key sequences.

Figure 17:
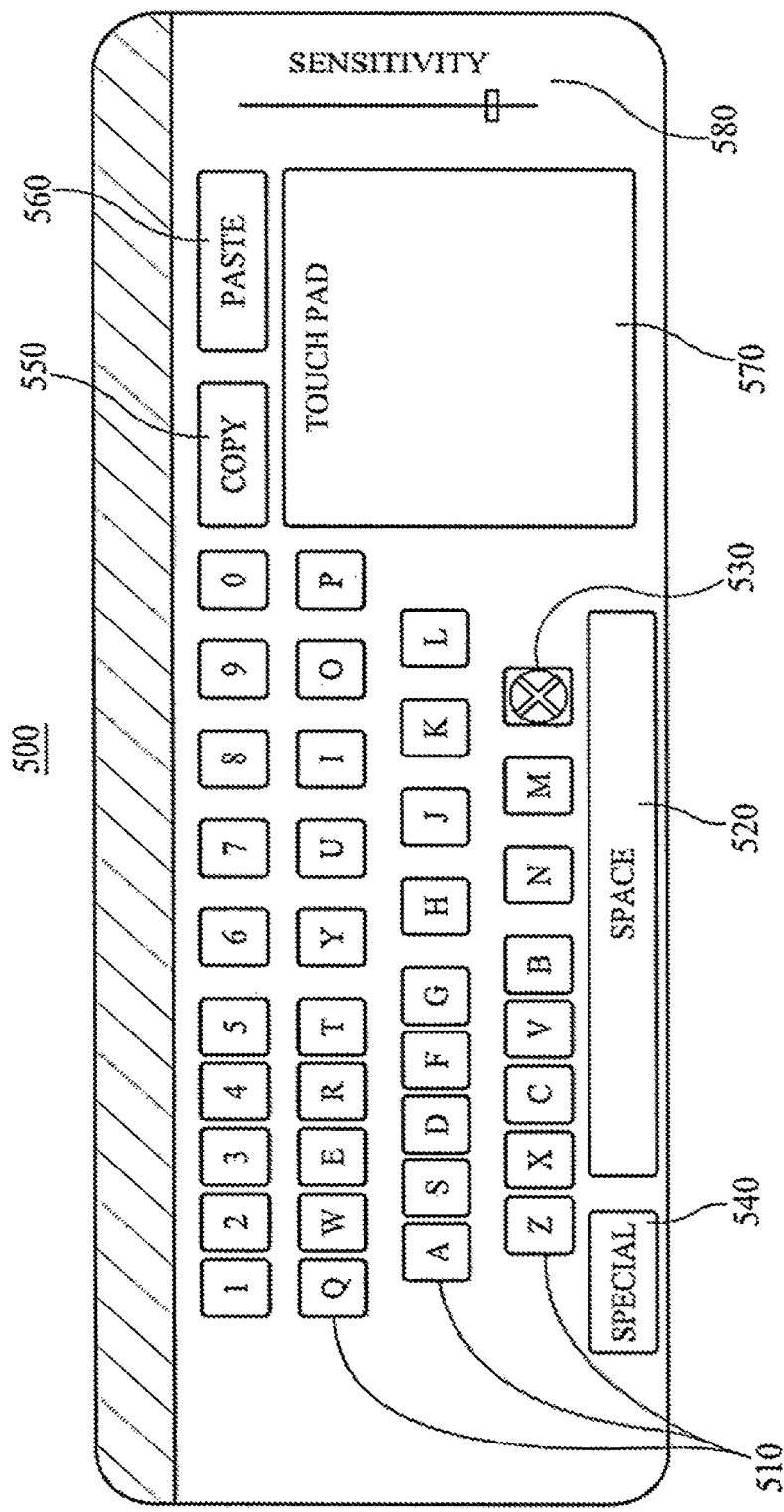
FIG. 17, is an illustration of a keyboard wherein horizontal spacings between keys mapped to the left hand are reduced, for users with limited metacarpophalangeal (digits/palm joint) or intercarpal (palm/wrist joint) articulation in the left hand, in accordance with an embodiment of the present invention.

Reference is made to FIG. 17, which is an illustration of a keyboard 1700 wherein horizontal spacings between keys mapped to the left hand are reduced, for users with limited metacarpophalangeal (digits/palm joint) or intercarpal (palm/wrist joint) articulation in the left hand, in accordance with an embodiment of the present invention. Keyboard 1700 limits travel distance between keys, enabling neighboring keys to be struck with minimal effort.

Figure 18:
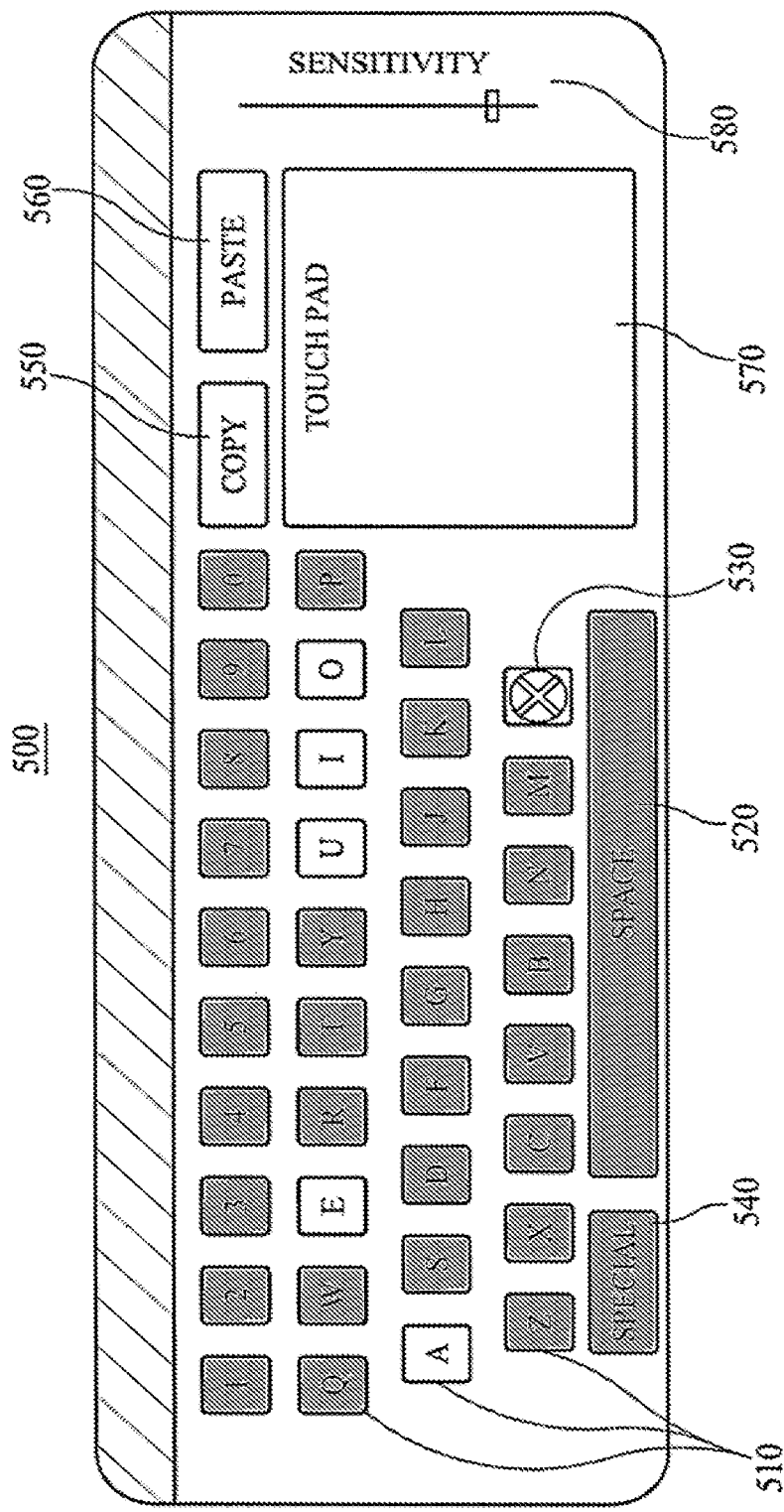
FIG. 18 is an illustration of a keyboard with keys that are selectively enabled and disabled to reduce typing errors and increase typing speed and comfort, for users that experience tremors in the hand such as user suffering from Parkinson's disease, and for users with limited motor accuracy such as users recovering from a stroke, in accordance with an embodiment of the present invention.

Reference is made to FIG. 18, which is an illustration of a keyboard 1800 with keys that are selectively enabled and disabled to reduce typing errors and increase typing speed and comfort, for users that experience tremors in the hand such as user suffering from Parkinson's disease, and for users with limited motor accuracy such as users recovering from a stroke, in accordance with an embodiment of the present invention. In FIG. 18 the accessibility module of the ONE KEYBOARD expects a vowel to be typed next. Only the vowel keys are active and able to be pressed, whereas input to non-vowel keys is disabled, depicted by the greyed-out consonants and digits in keyboard 1800.

Security is another major component of the ONE KEYBOARD. With the user's biometric template, the ONE KEYBOARD quickly detects when someone other than an authorized user is trying to access the system. Within a few lines of typing, the biometric template of the typist discriminates between an authorized user and an intruder. Companies interested in network security use this as a means of ensuring that only the correct user accesses each device. Common examples of this are on-line courses and test-taking, on-line e-commerce, and social networking companies who wish to prevent on-line bullying by "anonymous" users. Once the ONE KEYBOARD is attached to a computer, the driver can prevent anyone from detaching it and attempting to access the computer with a non-biometric keyboard. Currently, many behavioral biometric programs not only reject intruders, but they actually identify the intruder by their own behavioral biometric template. The time series generated by biometric analyzer 1600 is unique to each user and may be utilized as a digital identity.

The ONE KEYBOARD includes a cryptographic module 2300 (FIG. 1) that maps each user's time series to a cryptographic key. Cryptographic module 2300 generates a unique cryptographic key for each keyboard user. Each user key is used by that user to encrypt, securely transmit and digitally sign documents, and as a form of authentication in other applications, such as the secure shell protocol (SSH). Biometric encryption is already well-established for fingerprint and face, but thus far no one has tried to do so for keystroke dynamics. In this regard, reference is made to Colin Soutar, Danny Roberge, Alex Stoianov, Rene Gilroy and B. V. K. Vijaya Kumar, Biometric Encryption. In: Nickols, Randall K. (ed.) ICSA Guide to Cryptography, McGraw-Hill (1999).
http://www.cse.lehigh.edu/prr/Biometrics/Archive/Papers/BiometricEnc ryption.pdf Ann Cavoukian and Alex Stoianov A. (2011) Biometric Encryption. In: van Tilborg H. C. A., Jajodia S. (eds.) Encyclopedia of Cryptography and Security, Springer (2011), Boston, MA ISBN: 78-1-4419-5906-5 https://doi.org/10.1007/978-1-4419-5906-5 https://link.springer.com/referenceworkentry/10.1007%2F978-1-4419-4906-5 880

Protecting the user's privacy is another major feature of the ONE KEYBOARD. Keystroke dynamics is a technique that can be used to legitimately identify and authenticate a user by a trusted application, such as when logging into a secure banking website or during an online course. However, there are numerous scenarios in which a user's keystroke dynamics are exposed to an untrusted application. This dilemma is often encountered in web applications, whereby a single webpage may load dozens of third party modules that provide functionality through an external application programming interface (API). Given the lack of special permissions required to capture keyboard events in modern web browsers, an untrusted web application or third-party module can passively record the user's key press and release timings and use this information to track the user's identity. This presents a privacy concern since a malicious application can perform user identification and verification remotely via keystroke dynamics without the user's cooperation or knowledge. Since this type of attack relies only on the user's typing behavior, the user's identity may be compromised even when accessing the web application through an anonymizing network, such as The Onion Router (TOR). From this perspective, keystroke dynamics represents a form of "behavioral tracking", the process by which an advertiser or other third party is able to track user identity and demographics based on his online activity.

Obfuscation module 2000 (FIG. 1) of The ONE KEYBOARD mitigates this threat by masking the user's keystroke dynamics from any application which receives keyboard input. Obfuscation module 2000 introduces a small random delay to each key press, key release, and touch event by temporarily buffering the event on the device before releasing it to the host computer. The buffer duration is chosen in such a way so as to meet two criteria: 1) the user's keystroke dynamics appear obfuscated to any application that receives keyboard input, mitigating the possibility of an untrusted application from performing user identification or verification; and 2) maximize the responsiveness of the keyboard, introducing a delay that is unnoticeable to the user. The ONE KEYBOARD is the first keyboard designed to protect the user's privacy in real time with a random delay that adapts to the user's typing speed.

There are numerous legitimate uses of keystroke dynamics employed by trusted applications and the ONE KEYBOARD may preserve the intended functionality of these applications. Such behavioral biometric services are provided by companies including TypingDNA, Behaviosec, KeyTrac. The ONE KEYBOARD is compatible with all of these applications, granted they are trusted by the user. This functionality is provided through an application-specific permissions mechanism, whereby the user may choose to trust certain applications, granting them access to the user's un-obfuscated keystroke timings, while allowing other untrusted applications access only to the obfuscated keystroke timings.

Using the ONE KEYBOARD and its associated methodology, on-line learning sites such as Coursera of Mountain View, CA, and Khan Academy of New York, NY, testing companies such as The College Board of New York, NY, and ACT of Iowa City, IA, and any company seeking to verify/ authenticate users who are accessing their systems via a remote connection, will increase the security of their systems dramatically.

Reference is made to FIG. 19, which is a simplified flowchart of biometric analysis and authentication, in accordance with an embodiment of the present invention. At operation 1910, biometric identifier 1610 generates a behavioral profile and a biometric template of the user. At operation 1920 the user attempts to access a system using keyboard 100. At operation 1930 biometric authenticator 1620 identifies the user based on his biometric template. At operation 1940 biometric authenticator 1920 grants or restricts the user's access to the system, based on the user's biometric template.

At operation 1950 obfuscation module 2000 obfuscates the user's key press and release timings, to prevent suspicious applications from recording the user's key press and release timings and tracking the user's identity. Obfuscation of key press and release timings may be performed inter alia by temporarily buffering the key press and release events, thereby introducing buffer duration errors into the timings.

At operation 1960 biometric authenticator 1620 grants trusted applications access to the user's un-obfuscated key press and release timings. At operation 1970 biometric authenticator 1620 makes continuous decisions as to the identity and authenticity of the user, based on his biometric template. At operation 1980 biometric behavioral analyzer 1630 responds to the user's affective state by instructing projection system 140 to update the layout of keyboard 100. At operation 1990 behavioral learning machine 1640 adaptively updates the user's biometric template to compensate for template aging and changes in the environment.

An important component of the ONE KEYBOARD is software device driver 1000 for the keyboard, shown in FIG. 10, which contains the necessary calibration and settings for the keyboard to be customized for each user.

Biometric learning machine 1640 uses a biometric learning algorithm. This algorithm collects data from the keyboard and then utilizes that data to "learn" from each user's experiences. Typing mistakes tend to be repetitive, such as touching a certain key too lightly, or misspelling some specific words because of inverting the letters. If a user misspells a word repeatedly, the algorithm determines if the error is due to incomplete activation of a key, or due to another error such as inversion of letters. It then maintains a file of these learned experiences for each user and compensates for them, so that the user experiences an error-free interaction. Preferably, the learning algorithm is separate from the ONE KEYBOARD. At present, there are numerous commercial entities utilizing biometric data. The ONE KEYBOARD is compatible with all of these applications.

Over time, biometric learning machine 1640 determines which applications a user uses most of the time. The universal keyboard suggests optimal keyboard layouts, based on the applications used most of the time, which enable a user to decrease his number of keystrokes, and improve his efficiency and experience.

The ONE KEYBOARD comes with a device driver. In addition, there is a small program that allows the user to choose from standard keyboard layouts, or design his own custom layout, using a simple graphical interface. There is an error-correcting program that corrects typing errors, similar to SWIFTKEY®, developed and manufactured by TouchType Limited of London, UK. There is an optional cloud based service that includes better "learning" from the user's experiences, and security systems that ensure that each user matches their biometric security profile.

The ONE KEYBOARD is the most innovative change to human-computer interaction (HCI, http://en.wikipedia.org/wiki/Human%E2%80%93computer interaction) with desktop and laptop computers in the past decade, and is the last keyboard anyone will ever need to buy.

One having the benefit of the subject disclosure will appreciate that there are many variations of the keyboard of the subject invention. The present invention may be embodied in applications for cellular phones, including inter alia the IPHONE® and IPAD® manufactured by Apple Corporation of Cupertino, CA, and the ANDROID™ phones manufactured by Samsung Electronics Co., Ltd of Korea, using built-in technology of the phones to collect biometric data.

Furthermore, add-on components to the ONE KEYBOARD device driver make use of the behavioral data collected during operation. These components inter alia detect fatigue and stress, detect mental states and/or moods, and diagnose physical ailments such as arthritis and Parkinson's disease. As such, the ONE KEYBOARD may be used by qualified medical professionals. Alternatively, or additionally, such information may be used to determine when a person may be more likely persuaded by a particular type of advertisement.

In the foregoing specification, the invention has been described with reference to specific exemplary embodiments thereof. It will, however, be evident that various modifications and changes may be made to the specific exemplary embodiments without departing from the broader spirit and scope of the invention as set forth in the appended claims. Accordingly, the specification and drawings are to be regarded in an illustrative rather than a restrictive sense.

What is claimed is:

1. A secure keyboard, comprising:
   a controller;
   a blank translucent surface for use as an input device;
   a capacitive layer mounted underneath said blank translucent surface, enabling detection of touch location and pressure on said blank translucent surface;
   a projection system projecting a visual layout of keys of a keyboard on said blank translucent surface, the visual layout comprising either one or both of (i) ASCII character keys and (ii) graphical buttons;
   a handprint generator controlled by said controller and coupled with said capacitive layer that, upon a user placing his hand on said blank translucent surface, generates a user template describing the user's hand, the user template comprising a list of keyboard surface coordinates and corresponding pressures, and stores the user template; and
   a handprint analyzer controlled by said controller and coupled with said capacitive layer, with said handprint generator, and with a computing device, that authenticates an unknown user who asserts an identity by matching the unknown user's template, currently generated by said handprint generator, to the stored user template for the identity asserted by the unknown user, wherein:
      when no match is found, indicates that the unknown user is not authorized to use the keyboard or not previously enrolled for the keyboard; and
      when a match is found, receives user input from the unknown user in conformance with the projected layout of keys, and generates therefrom a time series of ASCII characters or button selections for input to the computing device.

2. The secure keyboard of claim 1 wherein the user template generated by said handprint generator further comprises a time series comprising times of interaction of the user's hand with said blank translucent surface, locations of the interaction at each time of interaction, and the amount of pressure applied to said blank translucent surface at each location and time of interaction.

3. The secure keyboard of claim 2 wherein the user template generated by said handprint generator comprises physiological measurements extracted from the time series.

4. The secure keyboard of claim 3 wherein the physiological measurements comprise one or more of (i) finger lengths, (ii) palm surface area, and (iii) hand arches.

5. The secure keyboard of claim 2 wherein the user template generated by said handprint generator comprises behavioral measurements extracted from the time series.

6. The keyboard of claim 5 wherein the behavioral measurements comprise one or more of (i) a pressure heatmap formed by the user's hand on said blank translucent surface, (ii) the first and last parts of the user's hand to make contact with said blank translucent surface, and (iii) vibrations experienced by the keyboard while the user's hand is held on said blank translucent surface.

7. The secure keyboard of claim 1 wherein said keyboard further comprises an inertial measurement unit (IMU) sensor sensing an acceleration experienced by the keyboard, and wherein the user template generated by said handprint generator further comprises the acceleration experienced by the keyboard at each time of interaction.

8. The secure keyboard of claim 1 wherein said handprint analyzer authenticates the unknown user in response to receiving an authentication request from an application that runs on the computing device, which the unknown user is attempting to use.

9. A keyboard, comprising:
a controller;
a blank translucent surface for use as an input device;
a capacitive layer mounted underneath said blank translucent surface, enabling detection of touch location and pressure on said blank translucent surface;
a projection system projecting a visual layout of keys of a keyboard on said blank translucent surface, the visual layout comprising either one or both of (i) ASCII character keys and (ii) graphical buttons;
a handprint generator controlled by said controller and coupled with said capacitive layer, that, upon a user placing his hand on said blank translucent surface, generates a user template describing the user's hand, the template comprising a list of keyboard surface coordinates and corresponding pressures, and stores the user template; and
a handprint analyzer controlled by said controller and coupled with said capacitive layer and with said handprint generator, that identifies an unknown user by comparing the unknown user's template, currently generated by said handprint generator, to a plurality of stored user templates, wherein when a match is not found then the unknown user is not identified.

* * * * *